(12) United States Patent
Hickman

(10) Patent No.: US 7,575,536 B1
(45) Date of Patent: Aug. 18, 2009

(54) METHOD AND APPARATUS FOR REMOTE INTERACTIVE EXERCISE AND HEALTH EQUIPMENT

(75) Inventor: Paul L. Hickman, Los Altos Hills, CA (US)

(73) Assignee: ICON IP, Inc., Logan, UT (US)

( * ) Notice: Subject to any disclaimer, the term of this patent is extended or adjusted under 35 U.S.C. 154(b) by 0 days.

(21) Appl. No.: 10/729,356

(22) Filed: Dec. 5, 2003

Related U.S. Application Data

(63) Continuation of application No. 09/690,701, filed on Oct. 16, 2000, now Pat. No. 6,808,472, which is a continuation of application No. 09/273,591, filed on Mar. 22, 1999, now Pat. No. 6,193,631, which is a continuation of application No. 08/766,513, filed on Dec. 13, 1996, now Pat. No. 6,059,692.

(60) Provisional application No. 60/008,603, filed on Dec. 14, 1995.

(51) Int. Cl.
*A63B 71/00* (2006.01)

(52) U.S. Cl. .................... 482/8; 482/4; 482/9; 482/901

(58) Field of Classification Search ................ 482/1–9, 482/51, 54, 57, 900–902; 600/300, 418, 600/520; 607/2, 19, 32; 434/247
See application file for complete search history.

(56) References Cited

U.S. PATENT DOCUMENTS 3,518,985 A 7/1970 Quinton (Continued)

FOREIGN PATENT DOCUMENTS

CN 1162495 A 10/1997

(Continued)

OTHER PUBLICATIONS

Winkler, William J., "Pumping Iron With a Digital Friend", Business Week, Dec. 18, 1995, pp. 78a.

(Continued)

*Primary Examiner*—Glenn Richman
(74) *Attorney, Agent, or Firm*—Workman Nydegger

(57) ABSTRACT

An exercise system includes a local system having an exercise apparatus and an associated local computer, where the local computer controls and monitors the operation and use, respectively, of the exercise apparatus. The system further includes a remote system having a remote computer, and a transmission medium including a telephone line that couples the local system to the remote system for data communication between the local system and the remote system. The remote system may receive local system data from the local system concerning the use of the exercise apparatus, and the local system may receive remote system data from the remote system concerning the operation of the exercise apparatus. The local computer preferably controls the operation of the exercise apparatus based upon a modifiable script stored in a read/write memory of the local computer, which can be updated by the remote system. A method for controlling an exercise apparatus includes running a modifiable script on a local computer to control the use and to monitor the operation of an exercise apparatus, and communicating with a remote system to provide the remote system with data concerning the use of the exercise apparatus. The script is stored in read/write memory of the local computer and remote system data received from the remote system may include at least a portion of a new script to be stored in the read/write memory of the local computer.

14 Claims, 9 Drawing Sheets

U.S. PATENT DOCUMENTS

| | | | |
|---|---|---|---|
| 3,602,502 A | 8/1971 | Hampl | |
| 3,802,698 A | 4/1974 | Burian et al. | |
| 3,845,756 A | 11/1974 | Olsson | |
| 3,903,613 A | 9/1975 | Bisberg | |
| 4,020,795 A | 5/1977 | Marks | |
| 4,112,928 A | 9/1978 | Putsch | |
| 4,151,988 A | 5/1979 | Nabinger | |
| 4,220,996 A | 9/1980 | Searcy | |
| 4,358,105 A | 11/1982 | Sweeney, Jr. | |
| 4,408,613 A | 10/1983 | Relyea | |
| 4,542,897 A | 9/1985 | Melton et al. | |
| 4,544,152 A | 10/1985 | Taitel | |
| 4,549,044 A | 10/1985 | Durham | |
| 4,556,216 A | 12/1985 | Pitkanen | |
| 4,571,682 A | 2/1986 | Silverman et al. | |
| 4,642,769 A | 2/1987 | Petrofsky | |
| 4,659,074 A | 4/1987 | Taitel et al. | |
| 4,687,195 A | 8/1987 | Potts | |
| 4,702,475 A * | 10/1987 | Elstein et al. | 273/445 |
| 4,708,337 A | 11/1987 | Shyu | |
| 4,708,837 A | 11/1987 | Baxter et al. | |
| 4,709,917 A | 12/1987 | Yang | |
| 4,757,495 A | 7/1988 | Decker et al. | |
| 4,763,284 A | 8/1988 | Carlin | |
| 4,765,613 A * | 8/1988 | Voris | 482/5 |
| 4,818,234 A | 4/1989 | Redington et al. | |
| 4,828,257 A | 5/1989 | Dyer et al. | |
| 4,837,157 A | 6/1989 | Turnell et al. | |
| 4,842,266 A | 6/1989 | Sweeney, Sr. et al. | |
| 4,842,274 A | 6/1989 | Oosthuizen et al. | |
| 4,848,737 A | 7/1989 | Ehrenfield | |
| 4,860,763 A | 8/1989 | Schminke | |
| 4,866,704 A | 9/1989 | Bergman | |
| 4,889,108 A | 12/1989 | Bond et al. | |
| 4,919,418 A | 4/1990 | Miller | |
| 4,925,183 A | 5/1990 | Kim | |
| 4,927,136 A | 5/1990 | Leask | |
| 4,934,694 A | 6/1990 | McIntosh | |
| 4,938,474 A | 7/1990 | Sweeney et al. | |
| 4,949,993 A | 8/1990 | Stark et al. | |
| 4,959,713 A | 9/1990 | Morotomi et al. | |
| 4,998,725 A | 3/1991 | Watterson et al. | |
| 5,020,795 A | 6/1991 | Airy et al. | |
| 5,054,774 A | 10/1991 | Belsito | |
| 5,062,632 A | 11/1991 | Dalebout et al. | |
| 5,067,710 A | 11/1991 | Watterson et al. | |
| 5,078,152 A | 1/1992 | Bond et al. | |
| 5,086,385 A | 2/1992 | Launey et al. | |
| 5,089,960 A | 2/1992 | Sweeney, Jr. | |
| 5,104,120 A | 4/1992 | Watterson et al. | |
| 5,113,427 A | 5/1992 | Ryoichi et al. | |
| 5,137,501 A | 8/1992 | Mertesdorf | |
| 5,145,475 A | 9/1992 | Cares | |
| 5,149,084 A | 9/1992 | Dalebout et al. | |
| 5,180,347 A | 1/1993 | Chen | |
| 5,195,935 A | 3/1993 | Fencel | |
| 5,201,772 A * | 4/1993 | Maxwell | 623/24 |
| 5,213,555 A | 5/1993 | Hood et al. | |
| 5,230,673 A | 7/1993 | Maeyama et al. | |
| 5,240,417 A | 8/1993 | Smithson et al. | |
| 5,243,998 A | 9/1993 | Silverman et al. | |
| 5,254,066 A | 10/1993 | Brown et al. | |
| 5,256,115 A | 10/1993 | Scholder et al. | |
| 5,277,678 A * | 1/1994 | Friedebach et al. | 482/70 |
| 5,290,205 A | 3/1994 | Densmore et al. | |
| 5,292,293 A * | 3/1994 | Schumacher | 482/4 |
| 5,299,810 A | 4/1994 | Pierce et al. | |
| 5,308,296 A | 5/1994 | Eckstein | |
| 5,308,300 A | 5/1994 | Chino et al. | |
| 5,313,942 A | 5/1994 | Platzker | |
| 5,314,391 A | 5/1994 | Potash et al. | |
| 5,318,487 A * | 6/1994 | Golen et al. | 482/5 |
| 5,318,491 A | 6/1994 | Houston | |
| D348,493 S | 7/1994 | Ashby | |
| 5,328,420 A | 7/1994 | Allen | |
| 5,328,422 A | 7/1994 | Nichols | |
| 5,335,188 A | 8/1994 | Brisson | |
| 5,352,166 A | 10/1994 | Chang | |
| 5,361,091 A | 11/1994 | Hoarty et al. | |
| 5,375,068 A | 12/1994 | Palmer et al. | |
| 5,382,209 A | 1/1995 | Pasier et al. | |
| 5,385,519 A | 1/1995 | Hsu et al. | |
| 5,385,520 A | 1/1995 | Lepine et al. | |
| 5,387,164 A | 2/1995 | Brown, Jr. | |
| 5,403,252 A | 4/1995 | Leon et al. | |
| 5,407,402 A | 4/1995 | Brown et al. | |
| 5,410,471 A | 4/1995 | Alyfuku et al. | |
| 5,410,472 A | 4/1995 | Anderson | |
| 5,433,679 A | 7/1995 | Szymczak et al. | |
| 5,435,799 A | 7/1995 | Lundin | |
| 5,451,922 A | 9/1995 | Hamilton | |
| 5,462,051 A | 10/1995 | Oka et al. | |
| 5,462,503 A | 10/1995 | Benjamin et al. | |
| 5,462,504 A | 10/1995 | Trulaske et al. | |
| 5,466,200 A | 11/1995 | Ulrich et al. | |
| 5,474,090 A | 12/1995 | Begun et al. | |
| 5,484,389 A | 1/1996 | Stark et al. | |
| 5,489,249 A | 2/1996 | Brewer et al. | |
| 5,512,025 A | 4/1996 | Dalebout et al. | |
| 5,527,239 A | 6/1996 | Abbondanza | |
| 5,535,664 A | 7/1996 | Rokowski | |
| 5,538,486 A | 7/1996 | France et al. | |
| 5,546,324 A | 8/1996 | Palmer et al. | |
| 5,547,439 A | 8/1996 | Rawls et al. | |
| 5,572,643 A | 11/1996 | Judson | |
| 5,584,779 A | 12/1996 | Knecht et al. | |
| 5,590,128 A | 12/1996 | Maloney et al. | |
| 5,591,104 A | 1/1997 | Andrus et al. | |
| 5,598,849 A | 2/1997 | Browne | |
| 5,600,310 A | 2/1997 | Whipple, III et al. | |
| 5,605,336 A | 2/1997 | Gaoiran et al. | |
| 5,619,412 A | 4/1997 | Hapka | |
| 5,619,991 A | 4/1997 | Sloane | |
| 5,626,539 A | 5/1997 | Piaget et al. | |
| 5,645,509 A | 7/1997 | Brewer et al. | |
| 5,655,997 A * | 8/1997 | Greenberg et al. | 482/5 |
| 5,663,951 A | 9/1997 | Danneels et al. | |
| 5,667,459 A | 9/1997 | Su | |
| 5,690,582 A | 11/1997 | Ulrich et al. | |
| 5,690,852 A | 11/1997 | Saito et al. | |
| 5,695,400 A | 12/1997 | Fennell, Jr. et al. | |
| 5,697,834 A | 12/1997 | Heumann et al. | |
| 5,702,323 A | 12/1997 | Poulton | |
| 5,704,875 A | 1/1998 | Tanabe | |
| 5,720,771 A | 2/1998 | Snell | |
| 5,722,418 A | 3/1998 | Bro | |
| 5,738,612 A | 4/1998 | Tsuda | |
| 5,743,833 A | 4/1998 | Watterson et al. | |
| 5,749,372 A | 5/1998 | Allen et al. | |
| 5,752,897 A | 5/1998 | Skowronski et al. | |
| 5,754,765 A | 5/1998 | Danneels et al. | |
| 5,759,199 A | 6/1998 | Snell et al. | |
| 5,771,354 A | 6/1998 | Crawford | |
| 5,777,678 A | 7/1998 | Ogata et al. | |
| 5,779,596 A | 7/1998 | Weber | |
| 5,785,630 A | 7/1998 | Bobick et al. | |
| 5,785,631 A * | 7/1998 | Heidecke | 482/5 |
| 5,810,696 A | 9/1998 | Webb | |
| 5,836,770 A | 11/1998 | Powers | |
| 5,838,906 A | 11/1998 | Doyle et al. | |
| 5,845,230 A | 12/1998 | Lamberson | |
| 5,854,833 A | 12/1998 | Hogan et al. | |
| 5,857,939 A | 1/1999 | Kaufman | |
| 5,865,733 A | 2/1999 | Malinouskas et al. | |

| | | |
|---|---|---|
| 5,873,369 A | 2/1999 | Laniado et al. |
| 5,880,677 A | 3/1999 | Lestician |
| 5,888,172 A | 3/1999 | Andrus et al. |
| 5,890,906 A | 4/1999 | Macri et al. |
| 5,890,995 A | 4/1999 | Bobick et al. |
| 5,905,442 A | 5/1999 | Mosebrook et al. |
| 5,909,544 A | 6/1999 | Anderson, II et al. |
| 5,911,132 A | 6/1999 | Sloane |
| 5,911,687 A | 6/1999 | Sato et al. |
| 5,916,063 A | 6/1999 | Alessandri |
| 5,917,405 A | 6/1999 | Joao |
| 5,929,748 A | 7/1999 | Odinak |
| 5,929,782 A | 7/1999 | Stark |
| 5,931,763 A | 8/1999 | Alessandri |
| 5,947,869 A | 9/1999 | Shea |
| 5,956,509 A | 9/1999 | Kevner |
| 5,961,561 A | 10/1999 | Wakefield, II |
| 5,964,701 A | 10/1999 | Asada et al. |
| 5,967,975 A | 10/1999 | Ridgeway |
| 5,993,356 A | 11/1999 | Houston et al. |
| 5,995,868 A | 11/1999 | Dorfmeister et al. |
| 5,997,476 A | 12/1999 | Brown |
| 6,010,451 A | 1/2000 | Clawson |
| 6,013,007 A | 1/2000 | Root et al. |
| 6,014,432 A | 1/2000 | Modney |
| 6,033,344 A | 3/2000 | Trulaske et al. |
| 6,042,519 A | 3/2000 | Shea |
| 6,050,822 A | 4/2000 | Faughn |
| 6,050,924 A | 4/2000 | Shea |
| 6,050,942 A | 4/2000 | Rust et al. |
| 6,053,737 A | 4/2000 | Babbitt et al. |
| 6,053,844 A | 4/2000 | Clem |
| 6,059,692 A | 5/2000 | Hickman |
| 6,066,075 A | 5/2000 | Poulton |
| 6,066,705 A | 5/2000 | Calderon et al. |
| 6,106,297 A | 8/2000 | Pollak et al. |
| 6,132,337 A | 10/2000 | Krupka et al. |
| 6,148,262 A | 11/2000 | Fry |
| 6,152,854 A | 11/2000 | Carmein |
| 6,152,856 A | 11/2000 | Studor et al. |
| 6,162,151 A | 12/2000 | Tani et al. |
| 6,162,189 A | 12/2000 | Girone et al. |
| 6,171,186 B1 | 1/2001 | Kurosawa et al. |
| 6,171,218 B1 | 1/2001 | Shea |
| 6,193,631 B1 | 2/2001 | Hickman |
| 6,211,451 B1 | 4/2001 | Tohgi et al. |
| 6,231,481 B1 | 5/2001 | Brock |
| 6,231,482 B1 | 5/2001 | Thompson |
| 6,244,988 B1 | 6/2001 | Delman |
| 6,251,048 B1 | 6/2001 | Kaufman |
| 6,312,363 B1 | 11/2001 | Watterson et al. |
| 6,322,451 B1 | 11/2001 | Miura |
| 6,356,856 B1 | 3/2002 | Damen et al. |
| 6,358,187 B1 | 3/2002 | Smith |
| 6,371,850 B1 | 4/2002 | Sonoda |
| 6,450,922 B1 | 9/2002 | Henderson et al. |
| 6,458,060 B1 | 10/2002 | Watterson et al. |
| 6,463,385 B1 | 10/2002 | Fry |
| 6,464,618 B1 | 10/2002 | Shea |
| 6,475,115 B1 | 11/2002 | Candito et al. |
| 6,497,638 B1 | 12/2002 | Shea |
| 6,503,173 B2 | 1/2003 | Clem |
| 6,582,342 B2 | 6/2003 | Kaufman et al. |
| 6,585,622 B1 | 7/2003 | Shum et al. |
| 6,601,016 B1 | 7/2003 | Brown et al. |
| 6,605,020 B1 | 8/2003 | Huang |
| 6,605,038 B1 | 8/2003 | Teller et al. |
| 6,616,578 B2 | 9/2003 | Alessandri |
| 6,626,799 B2 | 9/2003 | Watterson et al. |
| 6,634,992 B1 | 10/2003 | Ogawa |
| 6,638,198 B1 | 10/2003 | Shea |
| 6,645,124 B1 | 11/2003 | Clem |
| 6,648,798 B2 | 11/2003 | Yoo |
| 6,659,946 B1 | 12/2003 | Batchelor et al. |
| 6,687,535 B2 | 2/2004 | Hautala et al. |
| 6,689,057 B1 | 2/2004 | Shinsel et al. |
| 6,702,719 B1 | 3/2004 | Brown et al. |
| 6,736,759 B1 | 5/2004 | Stubbs et al. |
| 6,740,007 B2 | 5/2004 | Gordon et al. |
| 6,749,537 B1 | 6/2004 | Hickman |
| 6,783,482 B2 | 8/2004 | Oglesby et al. |
| 6,786,848 B2 | 9/2004 | Yamashita et al. |
| 6,790,178 B1 | 9/2004 | Mault et al. |
| 6,793,607 B2 | 9/2004 | Neil |
| 6,808,472 B1 | 10/2004 | Hickman |
| 6,808,473 B2 | 10/2004 | Hisano et al. |
| 6,824,502 B1 | 11/2004 | Huang |
| 6,825,876 B1 | 11/2004 | Easwar et al. |
| 6,863,641 B1 | 3/2005 | Brown et al. |
| 6,886,613 B1 | 5/2005 | Brown et al. |
| 6,918,858 B2 | 7/2005 | Watterson et al. |
| 6,921,351 B1 | 7/2005 | Hickman et al. |
| 6,991,586 B2 | 1/2006 | Lapcevic |
| 6,997,852 B2 | 2/2006 | Watterson et al. |
| 7,022,047 B2 | 4/2006 | Cohen et al. |
| 7,044,891 B1 | 5/2006 | Rivera |
| 7,056,265 B1 | 6/2006 | Shea |
| 7,060,006 B1 | 6/2006 | Watterson et al. |
| 7,060,008 B2 | 6/2006 | Watterson et al. |
| 7,070,539 B2 | 7/2006 | Brown et al. |
| 7,072,789 B2 | 7/2006 | Vock et al. |
| 7,115,076 B2 | 10/2006 | Oglesby et al. |
| 7,128,693 B2 | 10/2006 | Brown et al. |
| 7,166,062 B1 | 1/2007 | Watterson et al. |
| 7,166,064 B2 | 1/2007 | Watterson et al. |
| 7,254,516 B2 | 8/2007 | Case, Jr. et al. |
| 7,350,787 B2 | 4/2008 | Voss |
| 7,354,380 B2 | 4/2008 | Volpe, Jr. |
| 2004/0012335 A1 | 1/2004 | Shon et al. |
| 2004/0127335 A1 | 7/2004 | Watterson et al. |
| 2004/0162189 A1 | 8/2004 | Hickman |
| 2005/0233859 A1 | 10/2005 | Takai et al. |
| 2005/0233861 A1 | 10/2005 | Hickman et al. |
| 2005/0261609 A1 | 11/2005 | Collings et al. |
| 2006/0205566 A1 | 9/2006 | Watterson et al. |
| 2006/0205569 A1 | 9/2006 | Watterson et al. |
| 2006/0281603 A1 | 12/2006 | Hickman |
| 2007/0265138 A1 | 11/2007 | Ashby |
| 2008/0051256 A1 | 2/2008 | Ashby et al. |

FOREIGN PATENT DOCUMENTS

| | | |
|---|---|---|
| CN | 2449755 Y | 9/2001 |
| DE | 41 00 559 A1 | 7/1991 |
| EP | 0 199 442 | 10/1986 |
| JP | H10-243979 | 9/1998 |
| WO | WO 98/32496 | 7/1998 |

OTHER PUBLICATIONS

Internet Archive Wayback Machine, archive for www.ifit.com, at http://web.archive.org/web/*/www.ifit.com, Sep. 1, 2003, 1 pg.

iFIT.com "Internet workouts control your treadmill, bike, or elliptical", at http://www.ifit.com, Sep. 1, 2003, 3 pgs.

Icon Health And Fitness, Nordictrack C2420 (Model No. NTL 14950), 2004.

Icon Health And Fitness, Nordictrack C2420 (Model No. NTL 14951), 2004.

Icon Health And Fitness, Nordictrack C2420 (Model No. NTL 1459. 2), 2004.

Icon Health And Fitness, Nordictrack CX 990 (Model No. NEL 09940), 2003.

Icon Health And Fitness, Nordictrack SL 760 (Model No. NTC 89021), 2004.

Icon Health And Fitness, Nordictrack SL 760 (Model No. NTC 89020), 2004.

Icon Health And Fitness, Nordictrack SL 710 (Model No. NTC 07942), 2004.
Icon Health And Fitness, Nordictrack SL 710 (Model No. NTC 07941), 2004.
Icon Health And Fitness, Nordictrack SL 710 (Model No. NTC 07940), 2003.
Icon Health And Fitness, Nordictrack SL 705 (Model No. NTC 05941), 2004.
Icon Health And Fitness, Nordictrack SL 705 (Model No. NTC 05940), 2004.
Icon Health And Fitness, Nordictrack C2420 Manual preceding Specs, 2004.
Icon Health And Fitness, Pro-Form Personal Trainer Plus, undated.
Icon Health And Fitness, Screenshots of iFit.com, undated.
Icon Health And Fitness, iFit.com "Log on. Work out." Brochure, 2000.
Icon Health And Fitness, Website printouts (archived docs), 2000.
Pro Form Fitness Products Inc, Pro-Form 8.0 TXP Manual (for Model No. PF80010), Nov. 1991.
Pro Form Fitness Products Inc, Options Manual: Video Track / Track Five /Personal Trainer Plus (Part No. 109917), Sep. 1992, Pro Form Fitness Products, Inc.
Pro Form Fitness Products Inc, Lifestyler 10.0 ESP Manual (for Model No. 297052), Nov. 1992.
Icon Health And Fitness, Pro-Form 600 (Model No. PETL60000), 2000.
Icon Health And Fitness Inc, Reebok ACD1 (Model No. RETL11900), 2000.
Icon Health And Fitness Inc, Reebok RT1000 (Model No. RETL16001), 2001.
Icon Health And Fitness, Little Tony, One on One Video Trainer (for Model No. TLT23040), Jun. 1005.
Icon Health And Fitness Inc, One-on-One Video Trainer (Model No. TLTL21040), 1995.
Daniels, Virtual Workouts - Treadmills Possessed, Fortune Magazine, p. 84, Apr. 17, 2000.
Samiljan, Work Out Online, US Weekley, p. 71, Mar. 27, 2000.
Good Housekeeping, A Run for the Money, Good Housekeeping, p. 53, Feb. 2000.
Consumer Reports - Out of the Rat Race, onto a Treadmill, 2000.
Steinberg, Men's Journal, Squat.com, The Home Gym Goes Online, May 2000.
The Herald Journal, Icon Wins Awards, The Herald Journal, People in Business, vol. 91, No. 128, May, 7, 2000.
Stein, MSNBC.com, Smart Fitness Section, On a Quest for Fitness - The latest workout gear and Gadgets, Feb. 20, 2000.
ASP, New home excercise equipment: your computer?, Ebsco Publishing, Jun 2000.
Lehr, Wired Workout Local Gyms, The Boston Globe, Living Section, p. F1, Mar. 11, 2000.
Icon Health And Fitness, Turn Your Treamil into an Internet Appliance With www.iFit.com, PR Newswire, OCt. 19, 1999.
IEEE Computer graphics and Applications - EVAC: A Virtual Environment for Control of Remote Imaging Instrumentation, 1996.
Mercuris et al, Communications of the ACM, vol. 35, No. 6, The Distributed Laboratory, Jun. 1992.
IEEE: Performance Analysis of a Gateway Connecting the Cebus to the ISDN, 1993.
Wakita et al, IEEE Publication, Intelligent Monitoring System for Limited Communication Path: Telerobotic Task Execution over Internet, 0-8186-7108-Apr. 1995(IEEE), Apr. 1995.
Skubic et al, IEEE Publication, A Telerobotic Construction Set with Integrated Performance Analysis, 0-8186-7108-Apr. 1995(IEEE), Apr. 1995.
Fitness Equipment: Cardio, 1997.
Icon Health And Fitness Inc, Photographs of various fitness equipment systems, 1989-1996.
Madmoiselle, www.IFIT.com, Madmoiselle, Mar. 2000.
Wired, Icon Health & Fitness Image, 10.4Qi, Wired, Apr. 2000.
Cooking Light, Cybertrainers are Watching Your Workout, Cooking Light, Aug. 2000.
Villarosa, A Fitness Industry, With Gadgets Galore, The New York Times, Apr. 25, 2000.

Little, Web creates workouts with virtual trainers, The Birmingham News, Apr. 10, 2000.
San Francisco Chronicle, Let the Web Help You Get Physical, Mar. 16, 2000.
Pro Form Products Inc, 1994 Pro Form First in Fitness Brochure, 1994.
Icon Health And Fitness, Inc's Preliminary Invalidity Contentions, US Dist. CT. EDTX, case 2:05-cv-527, Jun. 16, 2006.
Icon Health And Fitness, Inc's Supplemental Preliminary Invalidity Contentions, US Dist. CT. EDTX, Case 2:05-cv-527, Jun. 23, 2006.
DVD Labeled "Icon-CYB001" 881 PDF Files Jun. 12, 2006.
CD-ROM Labeled "Supershow 2000", Icon-CYB 034309 Highlight Video Apr. 20, 2006.
CD-ROM Labeled "Supershow 1998", Icon-CYB 034310 Live Video Streaming from Logan Utah to Atlanta Georgia, Feb. 10, 1998.
DVD labeled "1998 supershow Web Cast" Icon-CYB 034311 Raw video footage . . . Jun. 2006.
CD-ROM Labeled "Steve Young Webcast", Icon-CYB 034312, Sales Meeting 2000, Jun. 2006.
*The FitLinxx Interactive Fitness Network™, Integrated Fitness Corp.*, brochure, 1998.
Fitlinxx Interactive Fitness Network™, *The Difference Between Surviving and Thriving May be as Simple as FitLinxx™, Intergrated Fitness Corp.*, brochure, 1998.
Forbes.com *Sweat equity*, www.forbes.com, Feb. 1998.
Netpulse, *Networkingout--Coming Distractions: Netpulse Helps Exercisers Surf the Net at the Gym, Accomplish Several Goals at Once*, www.netpulse.com, Apr. 1998.
Netpulse, *Instead of having an equipment repair technician traveling over hill and dale, you may soon have equipment repaired via the internet*, www.netpusle.com, Jul. 1998.
Netpulse, *Infotech is supposed to make life easier-remember? Here's how to be sure it does.*, www.netpulse.com, Aug. 1998.
Netpulse, Excersie station connects to the Net, *Now you can sweat to the Net.*, www.netpulse.com, Sep. 1998.
Netpulse, New Fitness Equipment Combines Internet, Sweat, *Now you can surf and sweat*, www.netpulse.com, Jan. 1999.
Netpulse, Hop In, Log On and Sweat, *Netpulse exercise machines are the latest Web feat*, www.netpulse.com, Feb. 1999.
Netpulse ClubWatch™, *Internet Powered Service,*, brochure, Apr. 1999.
Netpulse, *State of the Art*, www.netpulse.com, Feb. 2000.
Netpulse, *Netpulse Files for Patents on its Pioneering Technology Inventions and Groundbreaking Business Methods in the Media and Fitness Markets*, www.netpulse.com, May 2000.
Forbes, Digital Tool: Startups, *Sweat.equity*, www.forbes.com, Jun. 2000.
*Exergaming*, en.wikipedia.org, printed Oct. 1, 2007 (4 pages).
*WIRED*, www.wired.com, issue 2.09, Sep. 1994 (4 pages).
"Defendant's Amended Invalidity Contentions," Case No. 2:05-cv-527, Signed by Kirk Harris on Mar. 16, 2007 (15 pages).
"Expert Report of Dr. Brent Nelson Pursuant to Federal Rule of Civil Procedure 26(a)(2)(B)," dated Mar. 13, 2007 (372 pages).
"Netpulse Brings Free Internet Access to Fitness Center." Newsbytes.com, http://www.newsbytes.com, Jan. 17, 2000 (1 page).
"Precor and Netpulse Partner to Create the World's First Internet Powered Elliptical." Netpulse press release, Oct. 1, 1999 (2 pages).
"Surf While you Sweat." ABCNEWS.com, Oct. 27, 1998 (3 pages).
"The Best Products of 1999-Business Week's Top Picks of the Most Innovative Products on the Market," Business Week, Dec, 6, 1999 (2 pages).
Netpulse brochure. "Catch the wwwave," available on information and belief at least as early as Feb. 10, 2000 (6 pages).
*Consumer Reports, Out of the Rat Race, onto a Treadmill*, Feb. 2000 (5 pages).
*Consumer Reports, Out of the Rat Race, onto a Treadmill* at http://www.accemylibrary.com/coms2/summary_0286-28004514_ITM, Mar. 5, 2007, 8 pages.
DVD Labeled "iFIT.com Media Coverage News Clips Ver. 3.0," Mar. 30, 2000.
Office Action dated Sep. 11, 2000, 3 pages, U.S. Appl. No. 09/349,608.

Notice of Allowance and Issue Fee Date, date mailed Jul. 25, 2001, 2 pages, U.S. Appl. No. 09/349,608.
Notice of Allowance and Fee(s) Due, date mailed Sep. 20, 2004, 7 pages, U.S. Appl. No. 09/641,627.
Restriction Requirement dated Apr. 29, 2005, 4 pages, U.S. Appl. No. 09/641,627.
Office Action dated Jul. 26, 2005, 4 pages, U.S. Appl. No. 09/641,627.
Notice of Allowance and Fee(s) Due, date mailed Feb. 3, 2006, 4 pages, U.S. Appl. No. 09/641,627.
Notice of Allowance and Fee(s) Due, date mailed Sep. 1, 2006, 4 pages, U.S. Appl. No. 09/641,627.
Restriction requirement dated Aor. 17, 2007, 5 pages, U.S. Appl. No. 11/429,858.
Office Action dated Aug. 22, 2007, 5 pages, U.S. Appl. No. 11/429,858.
Restriction Requirement dated Feb. 5, 2008, 8 pages, U.S. Appl. No. 11/429,858.
Restriction Requirement dated Sep. 23, 2003, 4 pages, U.S. Appl. No. 09/641,600.
Office Action dated Feb. 11, 2004, 4 pages, U.S. Appl. No. 09/641,600.
Notice of Allowance and Fee(s) Due, date mailed Jun. 2, 2004, 4 pages, U.S. Appl. No. 09/641,600.
Office Action dated Feb. 15, 2005, 7 pages, U.S. Appl. No. 09/641,600.
Notice of Allowance and Fee(s) Due, dated mailed Sep. 14, 2005, 4 pages, U.S. Appl. No. 09/641,600.
Office Action dated Dec. 18, 2001, 3 pages, U.S. Appl. No. 09/641,220.
Notice of Allowance and Fee(s) Due, date mailed Jul. 1, 2002, 5 pages, U.S. Appl. No. 09/641,220.
Office Action dated Jun. 29, 2004, 3 pages, U.S. Appl. No. 09/776,410.
Notice of Allowance and Fee(s) Due, date mailed Nov. 12, 2004, 4 pages, U.S. Appl. No. 09/776,410.
Notice of Allowance and Fee(s) Due, date mailed Apr. 18, 2005, 5 pages, U.S. Appl. No. 09/776,410.
Restriction Requirement dated Oct. 9, 2007, 5 pages, U.S. Appl. No. 10/856,676.
Office Action dated Jan. 24, 2008, 5 pages, U.S. Appl. No. 10/856,676.
Restriction Requirement dated Jul. 1, 2003, 4 pages, U.S. Appl. No. 09/947,193.
Office Action dated Oct. 23, 2003, 4 pages, U.S. Appl. No. 09/947,193.
Notice of Allowance and Fee(s) Due, date mailed May 14, 2004, 4 pages, U.S. Appl. No. 09/947,193.
Office Action dated Sep. 15, 2005, 5 pages, U.S. Appl. No. 09/947,193.
Notice of Allowance and Fee(s) Due, date mailed Jan. 26, 2006, 5 pages, U.S. Appl. No. 09/947,193.
Notice of Allowance and Fee(s) Due, date mailed Aug. 16, 2006, 4 pages, U.S. Appl. No. 09/947,193.
Restriction Requirement dated Mar. 26, 2007, 5 pages, U.S. Appl. No. 11/429,725.
Office Action dated Jun. 6, 2007, 5 pages, U.S. Appl. No. 11/429,725.
Restriction Requirement dated Nov. 14, 2007, 5 pages, U.S. Appl. No. 11/429,725.
Final Office Action dated Feb. 28, 2008, 8 pages, U.S. Appl. No. 11/429,725.
Restriction Requirement dated Sep. 21, 2004, 4 pages, U.S. Appl. No. 10/106,824.
Office Action dated Nov. 12, 2004, 4 pages, U.S. Appl. No. 10/106,842.
Notice of Allowance and Fee(s) Due, date mailed Mar. 14, 2005, 6 pages, U.S. Appl. No. 10/106,842.
Notice of Allowance and Fee(s) Due, date mailed Mar. 29, 2006, 6 pages, U.S. Appl. No. 11/132,740.
Notice of Allowance and Fee(s) Due, date mailed Jun. 30, 2003, 5 pages, U.S. Appl. No. 09/933,701.
Restriction Requirement dated Aug. 22, 2006, 5 pages, U.S. Appl. No. 10/674,911.
Office Action dated Dec. 12, 2006, 7 pages, U.S. Appl. No. 10/674,911.
Restriction Requirement dated Jul. 2, 2007, 5 pages, U.S. Appl. No. 10/674,911.
Final Office Action dated Nov. 28, 2007, 8 pages, U.S. Appl. No. 10/674,911.
Office Action dated Apr. 22, 2008, 10 pages, U.S. Appl. No. 10/674,911.
Office Action dated Jun. 16, 1997, 4 pages, U.S. Appl. No. 08/766,513.
Office Action dated Feb. 17, 1998, 5 pages, U.S. Appl. No. 08/766,513.
Notice of Allowance and Issue Fee Due, date mailed Sep. 22, 1998, 3 pages, U.S. Appl. No. 08/766,513.
Response to Rule 312 Communication, dated Jun. 2, 1999, 2 pages, U.S. Appl. No. 08/766,513.
Office Action dated Dec. 10, 1999, 3 pages, U.S. Appl. No. 09/273,591.
Notice of Allowance and Fee(s) Due, date mailed Jul. 14, 2000, 2 pages, U.S. Appl. No. 09/273,591.
Office Action dated Dec. 18, 2001, 3 pages, U.S. Appl. No. 09/690,701.
Office Action dated Sep. 25, 2002, 4 pages, U.S. Appl. No. 09/690,701.
Final Office Action dated Mar. 21, 2003, 4 pages, U.S. Appl. No. 09/690,701.
Advisory Action dated Jun. 16, 2003, 2 pages, U.S. Appl. No. 09/690,701.
Notice of Allowance and Fee(s) Due, date mailed Nov. 24, 2003, 5 pages, U.S. Appl. No. 09/690,701.
Office Action dated Jan. 24, 2005, 4 pages, U.S. Appl. No. 10/773,617.
Notice of Allowance and Fee(s) Due, date mailed Apr. 17, 200, 4 pages, U.S. Appl. No. 10/773,617.
Notice of Allowance and Fee(s) Due, date mailed Jul. 6, 2006, 4 pages, U.S. Appl. No. 10773,617.
Office Action dated May 16, 2007, 4 pages, U.S. Appl. No. 10/773,617.
Office Action dated Jan. 24, 2008, 8 pages, U.S. Appl. No. 10/773,617.
Final Office Action dated Apr. 24, 2008, 10 pages, U.S. Appl. No. 10/773,617.
Office Action dated Dec. 18, 2001, 3 pages, U.S. Appl. No. 09/690,178.
Notice of Allowance and Fee(s) Due, date mailed Sep. 23, 2002, 5 pages, U.S. Appl. No. 09/690,178.
Office Action dated Mar. 7, 2003, 4 pages, U.S. Appl. No. 09/690,178.
Notice of Allowance and Fee(s) Due, date mailed Nov. 24, 2003, 4 pages, U.S. Appl. No. 09/690,178.
Response to Rule 312 Communication, dated Jan. 21, 2004, 2 pages, U.S. Appl. No. 09/690,178.
Office Action dated Jan. 27, 2005, 6 pages, U.S. Appl. No. 10/751,334.
Final Office Action dated Aug. 25, 2005, 6 pages, U.S. Appl. No. 10/751,334.
Notice of Allowance and Fee(s) Due, date mailed Jun. 12, 2006, 4 pages, U.S. Appl. No. 10/751,334.
Restriction Requirement dated Apr. 17, 2007, 5 pages, U.S. Appl. No. 10/751,334.
Restriction Requirement dated Aug. 9, 2007, 5 pages, U.S. Appl. No. 10/751,334.
Office Action dated Jan. 25, 2008, 7 pages, U.S. Appl. No. 10/751,334.
Office Action dated Jun. 15, 2004, 4 pages, U.S. Appl. No. 10/045,619.
Notice of Allowance and Fee(s) Due, date mailed Mar. 14, 2005, 4 pages, U.S. Appl. No. 10/045,619.
Restriction Requirement dated Jul. 27, 2006, 5 pages, U.S. Appl. No. 11/150,914.
Restriction Requirement dated Oct. 18, 2006, 5 pages, U.S. Appl. No. 11/150,914.

Office Action dated Feb. 22, 2007, 6 pages, U.S. Appl. No. 11/150,914.
Final Office action dated Dec. 12, 2007, 8 pages, U.S. Appl. No. 11/150,914.
Advisory Action dated Feb. 7, 2008, 3 pages, U.S. Appl. No. 11/150,914.
Final Office Action dated May 6, 2008 for U.S. Appl. No. 10/856,676, filed May 28, 2004.
Non-Final Office Action dated May 1, 2008 for U.S. Appl. No. 11/849,068, filed Aug. 31, 2007.
Restriction Requirement dated Apr. 28, 2008 for U.S. Appl. No. 11/150,914, filed Jun. 13, 2005.
Notice of Allowance and Fee(s) Due, date mailed Jun. 4, 2008, 8 pages, U.S. Appl. No. 11/429,858.
Notice of Allowance and Fee(s) Due dated Aug. 8, 2008, 4 pages, U.S. Appl. No. 11/429,858.
Notice of Allowance and fee(s) Due, date mailed Jun. 4, 2008, 9 pages, U.S. Appl. No. 11/429,725.
Notice of Allowance and Fee(s) Due dated Sep. 8, 2008, 4 pages, U.S. Appl. No. 11/429,725.
Final Office Action dated Jun. 2, 2008, 7 pages, U.S. Appl. No. 10/751,334.
Non-final Office Action dated Jun. 13, 2008, 6 pages, U.S. Appl. No. 11/657,701.
Non-final Office Action dated Jun. 26, 2008, 4 pages, U.S. Appl. No. 11/440,703.
Office Action dated Aug. 18, 2008, 9 pages, U.S. Appl. No. 10/674,911.
Office Action dated Aug. 21, 2008, 6 pages, U.S. Appl. No. 11/849,068.
Office Action Summary dated Nov. 25, 2008, 6 pages, U.S. Appl. No. 10/751,334.
Office Action Summary dated Oct. 16, 2008, 9 pages, U.S. Appl. No. 10/773,617.
Office Action Summary dated Jun. 27, 2008, 13 pages, U.S. Appl. No. 11/833,070.
Office Action Summary dated Oct. 31, 2008, 23 pages, U.S. Appl. No. 11/833,070.

* cited by examiner

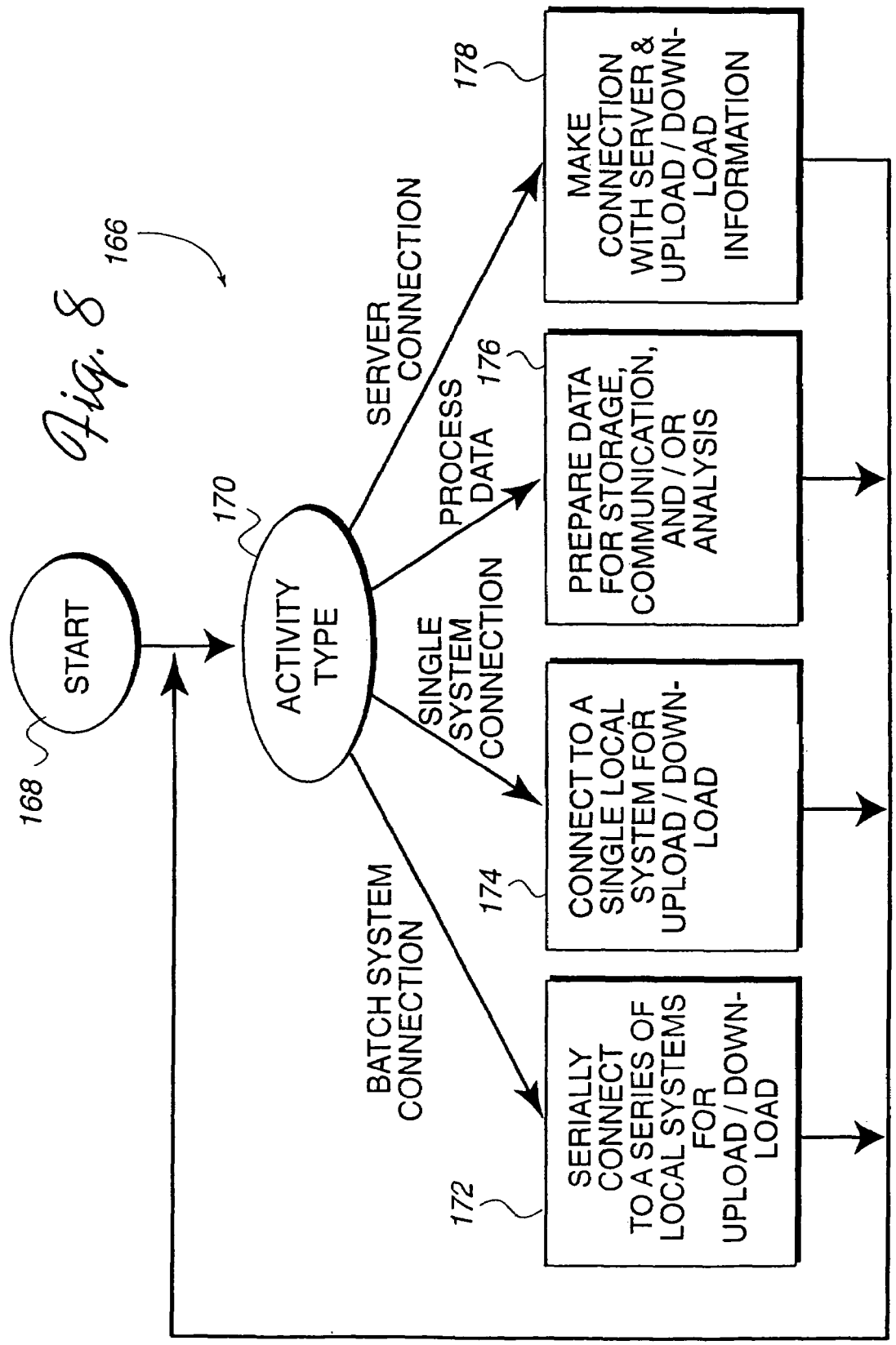

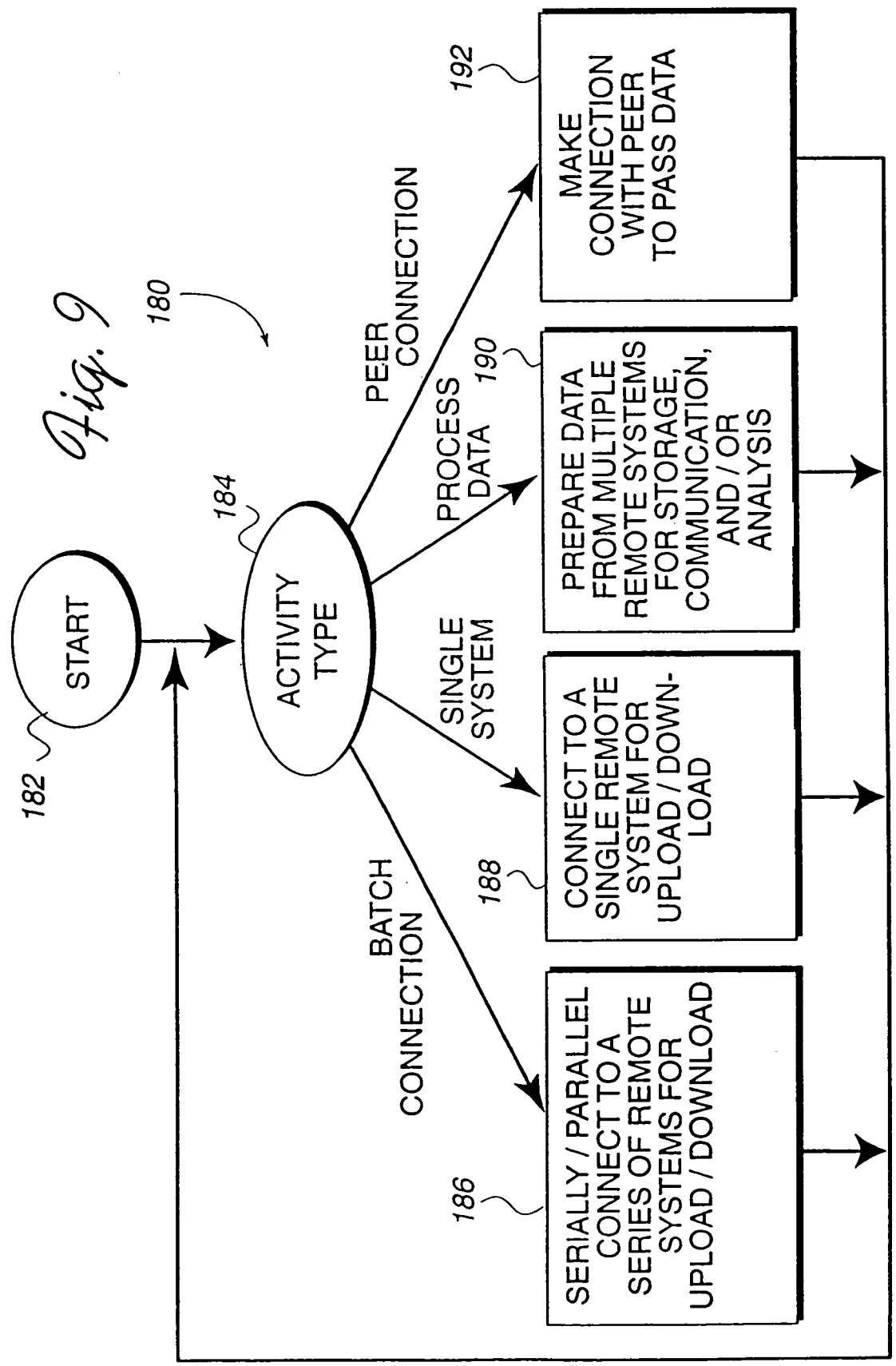

METHOD AND APPARATUS FOR REMOTE INTERACTIVE EXERCISE AND HEALTH EQUIPMENT

CROSS-REFERENCE TO RELATED APPLICATION

This application is a continuation of U.S. application Ser. No. 09/690,701, entitled METHOD AND APPARATUS FOR REMOTE INTERACTIVE EXERCISE AND HEALTH EQUIPMENT, filed on Oct. 16, 2000, now U.S. Pat. No. 6,808,472 which is a continuation of U.S. application Ser. No. 09/273,591, entitled METHOD AND APPARATUS FOR REMOTE INTERACTIVE EXERCISE AND HEALTH EQUIPMENT, filed on Mar. 22, 1999, now U.S. Pat. No. 6,193,631, which is a continuation of U.S. application Ser. No. 08/766,513, entitled METHOD AND APPARATUS FOR REMOTE INTERACTIVE EXERCISE AND HEALTH EQUIPMENT, filed on Dec. 13, 1996, now U.S. Pat. No. 6,059,692, which claims the benefit of U.S. application Ser. No. 60/008,603, entitled METHOD AND APPARATUS FOR REMOTE INTERACTIVE EXERCISE AND HEALTH EQUIPMENT, filed on Dec. 14, 1995.

BACKGROUND OF THE INVENTION

1. Field of the Invention

This invention relates generally to health and exercise equipment, and more particularly to computer networked systems including health or exercise equipment.

2. Description of the Related Art

Good health is a fundamental requirement for a happy and long life. A multi-billion dollar health and fitness industry has grown to help individuals meet this requirement. For example, there are a great many gymnasiums which provide facilities and equipment for aerobic and musculature development, and there are hundreds, if not thousands, of weight loss and diet centers and programs. The goals of these many programs typically includes weight loss and/or maintenance, the improvement of aerobic fitness, improved circulation, increased strength, and body building or shaping.

There are several problems encountered with the use of gymnasiums, fitness centers, and diet centers. For one, they tend to be fairly expensive due to the need to maintain the facilities, pay rent and payroll, buy equipment, etc. In addition, these centers tend to be inconvenient in that they require a special trip to the center by individuals wishing to use their facilities. Both the price and the inconvenience tend to discourage use of these centers over time, allowing the individuals to lose incentive and drop out of their fitness or diet program.

A partial solution to this problem is home exercise and health equipment. Again, a large industry has arisen to provide exercise and health equipment for the home. This equipment tends to be more of the aerobic type, e.g. stationary bicycles, rowing machines, "step" machines, etc., although weight lifting apparatus, sometimes referred to as "resistance trainers," are also widely used in the home. These types of home exercise and health equipment increasingly use sophisticated electronics, such as microprocessors, to monitor the level of exercise and to provide exercise programs for the user.

Unfortunately, even well designed home exercise and health equipment often fall into disuse over time. This is because individuals, even in their own home, often lack the incentive to exercise when there are other, more enjoyable, activities available. Also, since there is typically not the camaraderie often found in a health club, diet center, etc., it is easier for users, as individuals, to discontinue their exercise or diet program.

Personal trainers have been used both at fitness clubs and in the home. Personal trainers are individuals who usually have a fitness training background and who typically provide personal training services to an individual customers. Personal trainers can be very effective in that they provide personal motivation and feedback to an individual in the exercise program, and thus often foster a more effective and longer-lasting exercise program. The downside of personal trainers is, particularly in the home setting, their relatively high cost. It is not unusual for a personal trainer to charge hundreds of dollars per month for their services. Therefore, while these personal trainers are very effective, they tend to be used by only a small percentage of the population.

SUMMARY OF THE INVENTION

The present invention provides an exercise and health system which is convenient, affordable, and effective. The system includes computerized exercise and/or health equipment (the "local system") that can provide feedback and encouragement to the user, i.e. can serve as a "virtual personal trainer." In addition, the system includes a remote computer system communicating over a bi-directional data channel with the exercise and health equipment. Still further, the system can include a server computer system that is in communication with the remote computer systems to provide bi-directional data communication with the remote computer systems.

Since the exercise and health equipment can communicate with the user, it is possible for the health equipment to provide incentive and motivation to the user much in the same fashion as a human personal trainer. In addition, the health and exercise equipment can store data and other parameters concerning the exercise or other activities which can be used to monitor the progress and to vary the exercise program or script. In this way, the local system can serve as a "virtual personal trainer."

The remote system computer is preferably associated with a number of exercise and health locations. The remote system computer can be considered to be the communication tool of a human personal trainer, as opposed to the "virtual personal trainer" emulated by software in the local system computer. For example, the remote system computer can be associated with one hundred local systems (used by one or more individuals in, for example, their homes), and can be used to upload information from the exercise and health equipment of a local system to be analyzed by the personal trainer at the remote computer. The personal trainer can then call the individual user to provide additional instruction, encouragement, and cautions, and the remote system computer can download new exercise scripts or programs to the local system computer to implement these changes.

The server system computer serves a number of remote system computers. For example, while a remote system computer might serve one hundred local system computers, the server system computer might serve as one hundred remote system computers. The server system computer can communicate with other server system computers ("peer" servers), or with a yet higher order server system computers for the consolidation, storage, processing, and exchange of data. The server system computer can be used to communicate with the remote system computers for the uploading of data concerning the remote system computer and the local system computers that the remote system computer is in contact with, and it can also download new programs and other data and information to the remote system computers. For example, a server system computer or peer system computer might design a dietary program for a particular user which is then downloaded into the remote system computer for subsequent communication to the individual user of a local system.

The systems, methods, and apparatus of the present invention therefore can provide an effective exercise, dietary, and health program for a great number of individuals. The computerized health equipment provides incentive and encouragement to stay in the program, due to the "virtual personal trainer" of the local system, the human personal trainer of the remote system, and by the various services provided by the enterprise as a whole as supported by the server systems, peer systems, etc. For example, a variety of services of products can be offered to the users of the system to further their health and fitness goals.

These and other advantages of the present invention will become apparent upon the rating of the following descriptions and the study of the figures of the drawings.

BRIEF DESCRIPTION OF THE DRAWINGS

FIG. 8 is a flow diagram of a process running on a remote system computer of the present invention;

FIG. 9 is a flow diagram of a process running on a server system computer of the present invention.

DETAILED DESCRIPTION OF THE PREFERRED EMBODIMENTS

Figure 1:
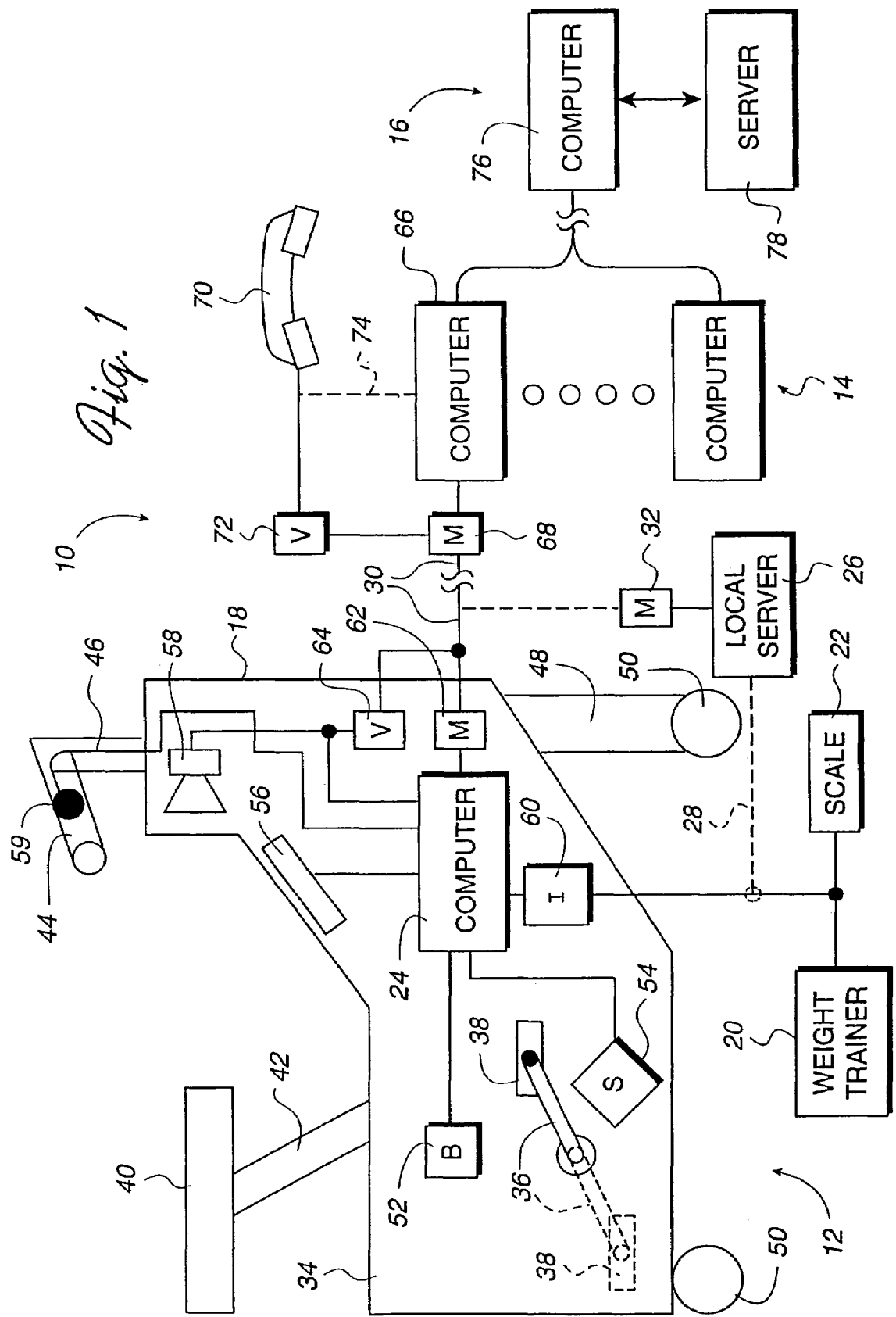
FIG. 1 is a block diagram of a health and fitness system in accordance with the present invention.

In FIG. 1, a health and fitness system 10 in accordance with the present invention includes one or more local systems 12, one or more remote systems 14, and one or more server systems 16. The local systems 12 are typically home-based systems designed for the promotion of the health and fitness of individual users within a family. The remote systems 14 may be home or business based, and are used as data gathering and storage stations, as well as communication stations, between a human personal trainer and users of local systems 12. As will be discussed in greater detail subsequently, the remote system 14 is associated with a relatively large number of local systems 12, e.g. a personal trainer with a remote system might be in communication with 100 or more individual users of local systems 12. This is made possible, in part, by providing a "virtual personal trainer" at each of the local stations 12 to partially or fully replace the need for a human personal trainer at the local station. The server systems 16 can communicate with the remote systems 14 to provide server and control functions across the entire enterprise, i.e. over the entire system 10. As also will be discussed in greater detail subsequently, the server system 16 is associated with a number of remote systems 14.

The local system 12 includes one or more health or fitness devices such as a stationary bicycle 18, a weight or "resistance trainer" 20, a scale 22, etc. Associated with a local system 12 is a computer 24 which, in this preferred embodiment, is integrated into the stationary bicycle 18. A stationary bicycle as a "base unit" is given merely by way of example, as any piece of equipment (a rowing machine, a step machine, etc.) could house the computer 24, or the computer 24 could be housed separately. The computer 24 can serve as a "local server" for other health and fitness devices at local system 12, such as the weight trainer 20 and the scale 22. Alternatively, a separate local server 26 can be used to control and/or support various devices in local system 12 via data and control lines 28, and communicate with the remote system 14 via a telephone line 30 and a modem 32. However, in the present preferred embodiment, the assumption is that the local server 26 and modem 32 are not required and that the computer 24 will serve not only to control the operation and data gathering function of the stationary bicycle 18, but will also provide these functions for the weight trainer 20 and the scale 22. Of course, the weight trainer 20 and the scale 22 may include their own computer systems for local control purposes.

The stationary bicycle 18 includes a housing 34 which, as stated previously, preferably houses the computer 24, a crank 36 provided with a pair of pedals 38, a seat 40 supported by a seat stem 42, handle bar 34 supported by handle bar stem 46, legs 48, and feet 50. The various components of the stationary bicycle 18 are typically attached to a rigid frame that is internal to the housing 34.

The weight trainer 20 is preferably a resistance-type weight trainer, such as a bench press machine, a biceps curl machine, a squat machine, etc. Typically the use grasps a bar connected to a cable that is attached to a resistance device. This resistance device can be weights, or can be an active resistance device such as a motor, or a passive resistance device such as an electrically actuated brake. In any event, the amount of resistance to movement of the bar is preferably under the control of the computer 24 and the script that it is running. The scale 22 preferably provides an electrical connection to the computer 24 through an I/O port to allow the computer 24 to monitor the weight of the person standing on the scale.

The computer 24 is coupled to a variety of input/output (I/O) devices including a brake 52, a sensor 54, a display 56, a heart rate monitor (HRM) 59, a loudspeaker 58, an interface 60, a modem 62, and a voice board 64. In this fashion, the computer 24 can control and monitor the various functions of the stationary bicycle 18.

More particularly, computer 24 can, under software and hardware control, control the electrically actuated brake 52 which is coupled to the crank 36 of the stationary bicycle. In this fashion, the pedaling force that must be exerted on pedals 38 to cause the crank 36 to rotate at a given speed can be varied under computer control. This electrically actuated brake can be electric/mechanical brake, electric/magnetic brake, etc. as it is well known to those skilled in the art. The sensor 54 is typically used to determine the rotations-per-minute (RPM) of the crank 36. In this way, the computer 24 can receive information concerning the level of effort being exerted by a user of the stationary bicycle 18. Rotation sensors are well known those skilled in the art. The sensor 54 can also measure other parameters such as the force (torque) being applied to pedal 38, again to provide information to the computer as to the level of effort being exerted by the user of the bicycle.

The computer can provide an output on a display 56 that can be viewed by an individual user sitting on seat 40. This display can be a simple light display, e.g. a series of light emitting diodes (LEDs) or it can be a full video display. A preferred embodiment of the present invention provides a full video display to provide instructions and encouragement to a user of the stationary bicycle. For example, an image of a "virtual personal trainer" can be provided on the video display 56. This image is preferably the image of the human personal trainer who is in charge of the remote system 14.

The loudspeaker 58 provides another important communication medium to the user of the stationary bicycle 18. For example, under computer 24 control, the user can be told with either a digitally synthesized or digitally recorded voice to pedal faster, pedal slower, that they are doing a good job, etc. Of course, analog recording techniques can be used as well, but are considered to be less flexible and desirable. Preferably, the voice being used is that of the personal trainer associated with the remote system 14 that oversees that local system 12. Both voice synthesis and digital voice recording on computer systems 24 are well known to those skilled in the art.

A local interface 60 can be used to couple the computer 24 to additional health and fitness devices. In this instance, the local interface 60 is coupled to the weight trainer 20 and to the scale 22. This additional health and fitness systems can either "dumb" systems with limited digital computation and storage capabilities, or they can include full fledged computer system such as the computer system 24. In the present embodiment, the weight trainer 20 and scale 22 include digital control circuitry (e.g. a microcontroller) which can communicate with the more powerful computer 24 of the stationary bicycle 18. The various I/O devices, such as the loudspeaker 58 can be used in conjunction with these other devices 20 and 22, e.g. the weight detected by the scale 22 can be announced on the loudspeaker 58 along with an indication that this is an increase or decrease in weight from the last session. Also, as mentioned previously, the weight trainer 20 can include the equivalent of the electrically control brake 52 which allows the resistance of the weight bar or handle to be varied to provide resistance ("weight") training. This control of the break within the weight trainer 20 can be controlled by a "script" of the computer 24.

The computer 24 is also coupled to a modem 62 for communication over a telephone line 30. Alternatively, the computer 24 can be coupled to the remote computer 14 by other communication linkages, such as ISDN digital transmission line, via a local area network, or via a wide area network (WAN) such as the Internet. In other words, the telephone line 30 represents only one type of data communication channel between the local systems 12 and the remote system 14. The present embodiment also includes a voice board 64 which can bypass the modem such that the loudspeaker 58 can be driven directly to the telephone line 30 in an analog fashion. Combination modem/voice boards are commercially available for personal computer systems, and are well known to those skilled in the art.

The remote system 14 includes, for example, a remote system computer 66 which is coupled to the telephone line 30 by a modem 68. In addition, a telephone 70 can be coupled to the line 30 by a voice board 72. Alternatively, the telephone 70 can be coupled to a separate telephone line so that simultaneous telephone and data links can be made. Still further alternatively, it is known to those skilled in the art that a single telephone line can be made to support both voice and data transmission. In any event, the telephone 70 can communicate directly with the loudspeaker 58 of the stationary bicycle 18 over the standard analog telephone line 30. Alternatively, the telephone 70 can communicate with the computer 66 as indicated by the broken line 74 and the computer 66 can communicate digital voice data via modem 68, telephone line 30 and modem 62, to the computer 24. The computer 24 can then store or pass through the digital voice data and play the voice input to the user of local station 12 via speaker 58.

As noted above, the computer 66 is used to communicate with the local system 12 via computer communication link such as the telephone line 30 or an equivalent. This communication can include the downloading of data and instructions to the computer 24, and can include the uploading of information from the computer 24 to the computer 66. This allows for interactive communication between the remote system 14 and the local systems 12.

The server stations 16 are used to further consolidate information from multiple remote system 14 and to provide a variety of services to the remote systems 14. While the remote system 14 maybe housed in human personal trainer homes or work sites, the server system(s) 16 are preferably more regional or national in origin. In this way, the main office of the enterprise can access each of the server systems 16 to provide upgrades for software, exercise programs, exercise equipment scripts, etc., as well as receiving information from the remote computers 66 that can be used for further analysis and for providing further services. Part of this analysis can be on the general and specific level of fitness of various individual users of the local system 12, as well as marketing information that can be used to offer product and services particularly tailored for the various users of the local system 12. The performance of the human personal trainers at remote stations 14 can also be monitored. It should be noted that the server 16 can include direct connect server 76 and peer server 78 that can either be direct server itself (like server 76) to a number of remote stations 14, or which can be a specialized server (such as a dietary analysis server) coupled to one or more direct connect servers 76. In addition, higher-level servers can be used to further consolidate data from the direct connect servers 76 and/or the peer servers 78. For example, the direct connect servers 76 can be regional in scope, while higher level servers can be national or international in scope.

Figure 2:
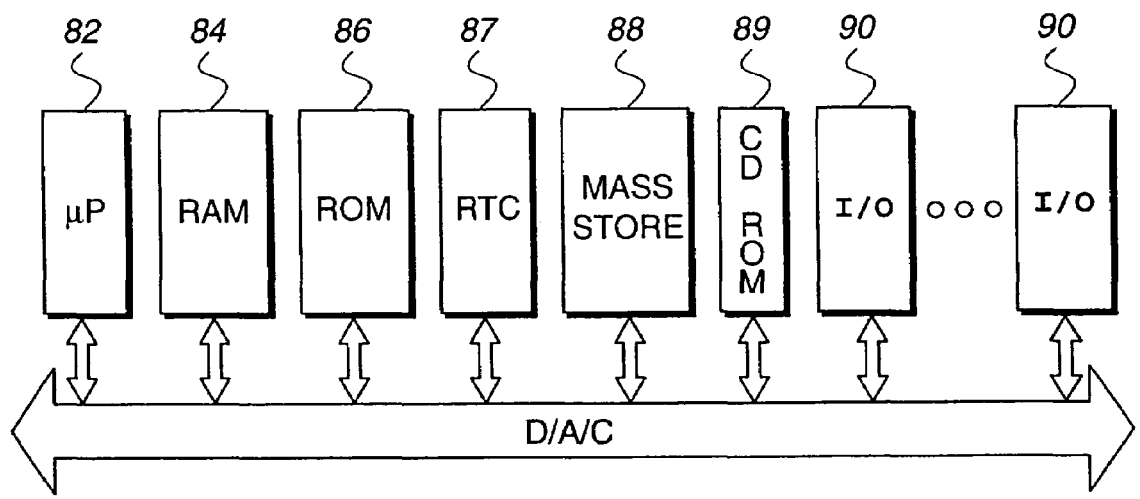
FIG. 2 is a block diagram of the local, remote, and server system computers of the present invention.

In FIG. 2, a computer 80 is shown in a block diagram form. This basic computer architecture can be used for the local system computer 24, the remote system computer 66, and the server system computer 76. Of course other and equivalent architectures (in the computational sense), such as parallel processing computers can be used in the present invention as well. In the disclosed embodiment, the computer 80 includes a microprocessor 82, random access memory (RAM) 84, read only memory (ROM) 86, real time clock (RTC) 87, digital mass storage 88, CD-ROM drive 89, and a number of input/output (I/O) ports 90. Preferably, the digital mass storage 88 is read/write memory such as a hard disk with adequate storage capacity (e.g. 40 megabytes to 2 gigabytes or more). In addition, CD-ROM drive 89 can be coupled to the bus to provide, in particular, images to be displayed on a display 56 of the local system 12. The various components 82–90 address, pass data, and pass control signals through a bus 92 which typically includes data (D), address (A), and control (C) lines, as it is well known to those skilled in the art. In addition, there are control and "glue" chips typically provided in the form of a "chipset" which are used to couple the various components of the system together. The design and manufacture of computer systems such as computer system 80 is well known to those skilled in the art, and such computer systems are commercially available, both as complete systems and as subsystems (e.g. motherboards) from a variety of commercial sources.

Figure 3:
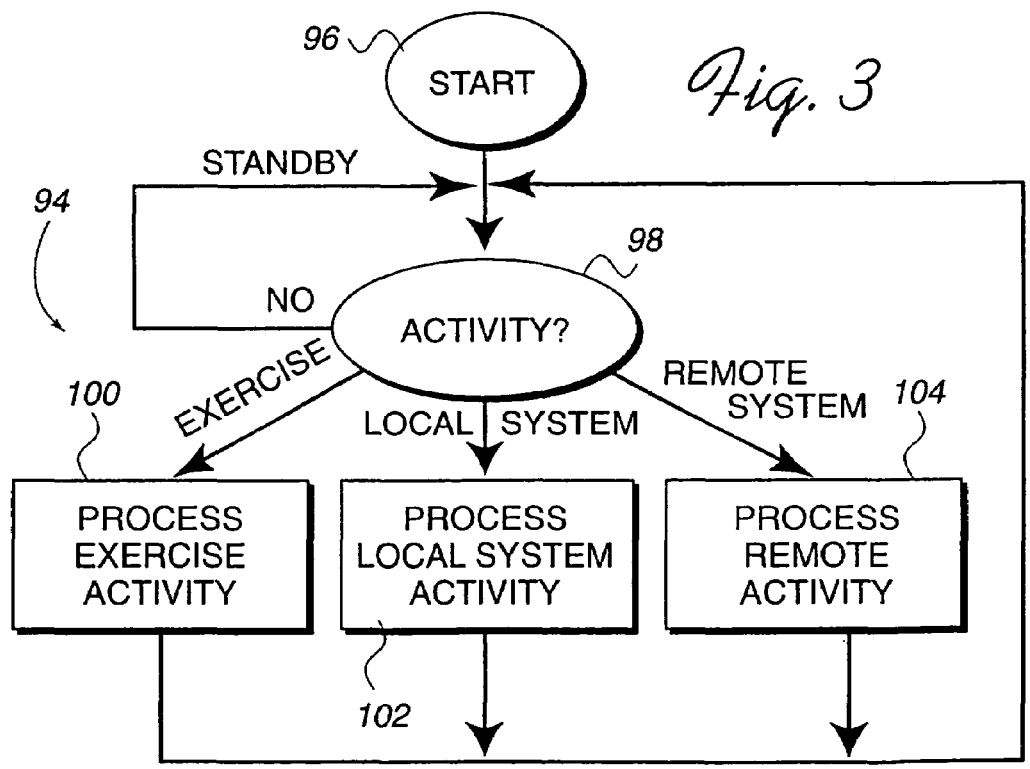
FIG. 3 is a flow diagram of a process running on a local system computer of the present invention.

In FIG. 3, a process 94 implemented on a local system computer 24 is illustrated in a flow diagram. The process begins at 96 and, in a decision step 98, it is determined whether there is any activity which requires the attention local system computer. If not, the computer system 24 is in a "standby" mode and process control is returned to step 98 in a recurring manner. If step 98 does determine that there is some activity, one or more of multiple branches are made to process the activity. If the activity is "EXERCISE", e.g. the stationary bicycle 18, the weight trainer 20, or the scale 22 is to be used, a step 100 processes the exercise activity. If it is a "LOCAL SYSTEM" activity such as routine housekeeping, the local system activity is processed in a step 102. If it is a "REMOTE SYSTEM" activity, the remote system activity is processed in a step 104. After the completion of any one of steps 100, 102, and 104, process control is returned to step 98. Of course, other types of activities can be initiated by step 98 such as, for example, a shut down activity which would cause a power-down of system, as will be appreciated by those skilled in the art.

Figure 4:
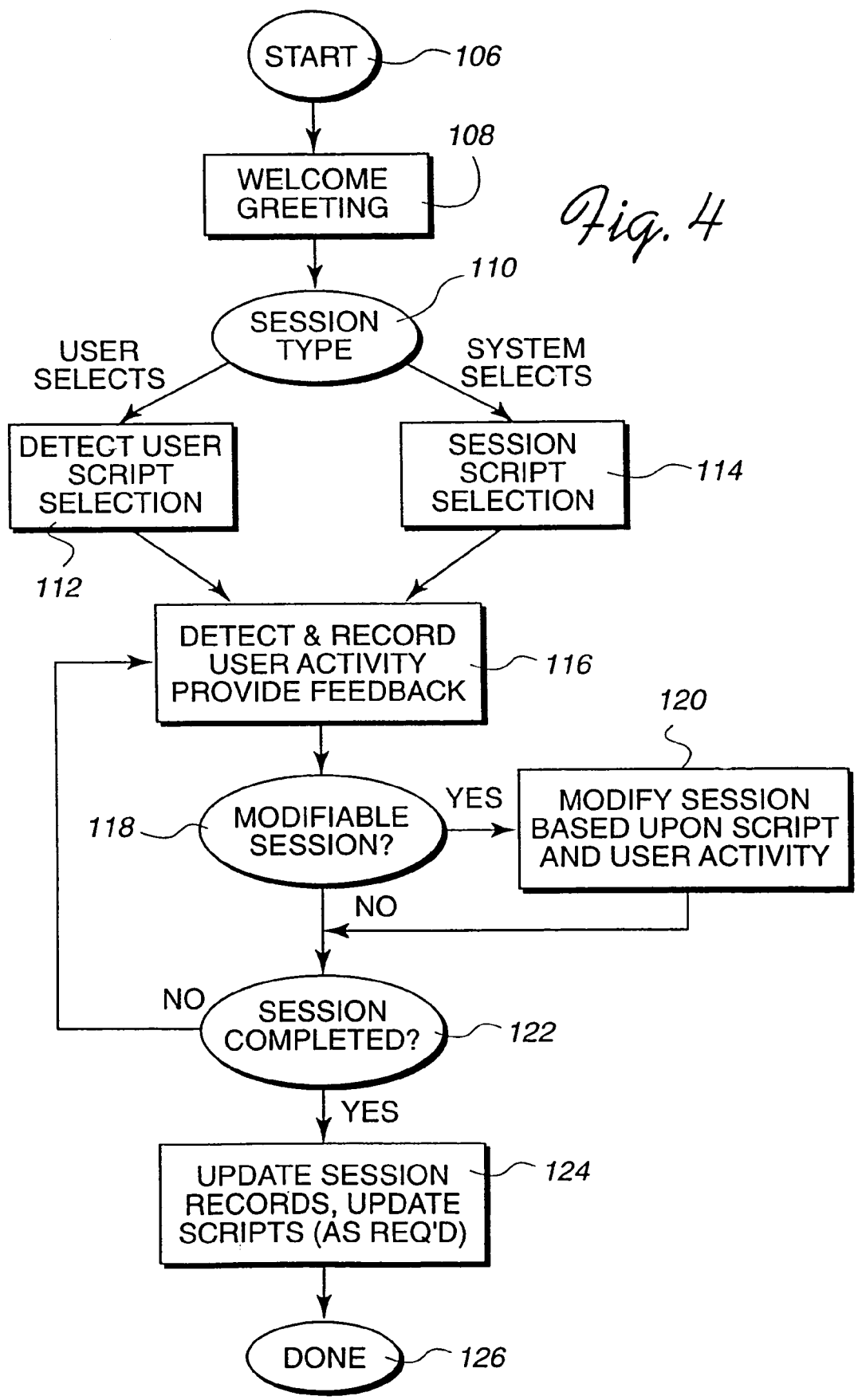
FIG. 4 is a flow diagram of the "PROCESS EXERCISE ACTIVITY" step of FIG. 3.

In FIG. 4, step 100 of FIG. 3 is illustrated in greater detail. The process 100 begins at step 106 and, in a step 108, a "welcome greeting" is created. This welcome greeting can be displayed on the screen 56 and/or can be heard from the speaker 58, and can be personalized to both the individual user of the local system 12 and the human personal trainer of remote station 14. For example, the image of the personal trainer can show up on the screen 56 with his voice saying "Good morning, Fred! I haven't seen you since last Wednesday. Let's try to get in a good work-out today!" This greeting forms a part of a "virtual personal trainer" at local system 12 which replaces some or all of the need for a human personal trainer to be present at the exercise session at the local system 12. The "virtual personal trainer" is, therefore, a computerized process which emulates part or all of the functions traditionally performed by a human personal trainer.

Next, in a selection step 110, the user decides whether he wants to select his own training program for that session or if he would like the system 12 to select the program. If the user selects the program, he creates a user "script" of what kind of exercise program he would like to perform that day. For example, if the user wishes to simply bicycle at a fixed resistance for thirty minutes, that can be entered in step 112. Alternatively, more complex "scripts" can indicate that he would like to bicycle with interval training for thirty minutes, and then do five repetitions on the weight trainer 20.

If, however, the user allows the system 12 to select the section type, step 114 controls the script selection. This is the preferred mode for using the local station 12 in that the script can be influenced not only by the local station 12, but also by the human personal trainer at the remote system computer 66. For example, data concerning the user's previous performances and the personal trainer's guidance can be stored in mass storage 88 (e.g. on a hard disk) so that a custom-tailored, interactive exercise program can be provided.

As noted above, the exercise program preferably proceeds according to "scripts." A script is simply a sequence of exercise or other health-related events that are performed in fixed or variable sequences. The order and structuring of the script can be modified based upon monitoring the user's performance or by other user feedback. For example, if it is detected that the user is getting tired due to a slowing of the exercise repetition rate, the steps or parameters of the exercise script can be modified accordingly. In other words, certain script steps can be skipped or the parameters concerning the steps can be modified. For example, if a user is determined to be tiring by the local system 12, and if the script says the next exercise event is to be ten repetitions on the weight trainer 20, that step could be skipped. Alternatively, the weight training step could still be done, but the resistance parameters could be modified. For example, instead of doing ten repetitions at a hundred pounds resistance on the weight trainer 20, eight repetitions at eighty pounds of resistance might be called for. The script therefore provides a general framework of a desired exercise session which can be varied based upon human personal trainer input from remote system 14, user input at local station 12, and detected user performance at local station 12.

Once the script has been initiated in either steps 112 or 114, a step 116 detects and records user activity and provides feedback to the user. This step will be discussed in greater detail subsequently. Such parameters as the rotations per minute (RPM) of the crank 36, the timing and speed of the resistance weight repetitions of weight trainer 20, the detected weight on the scale 22, etc. can all be recorded in the mass storage 88 of the local system computer 24. In addition, user feedback is provided. For example, if the person is cycling too slow on the stationary bicycle 18, the computer 24 can generate a encouragement on speaker 58 that the person should pedal faster. Alternatively, if it is determined that the user is over-exerting, such as pedaling too fast, a cautionary warning can be issued on speaker 58 to slow down. Another important input is the heart rate monitor (HRM) 59 which detects if the heart (pulse) rate is rising too high.

Next, in a step 118, it is determined whether the session is a modifiable session. Most sessions are preferably be modifiable, unless the user selects, in a step 112, a non-modifiable session. If the session is modifiable, the session is modified in a step 120 based upon the selected script and upon user activity or other input. For example, if the heart rate monitor 59 detects that the pulse rate is too high, the resistance on the crank 36 can be reduced via a signal to the brake 52. Next, in a step 122, it is determined whether the session is completed. This is usually based on the script, although the user can always terminate a session. If the session is not completed, process control is returned to step 116 to repeat the loop. If the session is completed, the session records are updated in the mass storage 88, as are the scripts, as indicated in step 124. The process 100 is then completed at step 126.

Figure 5:
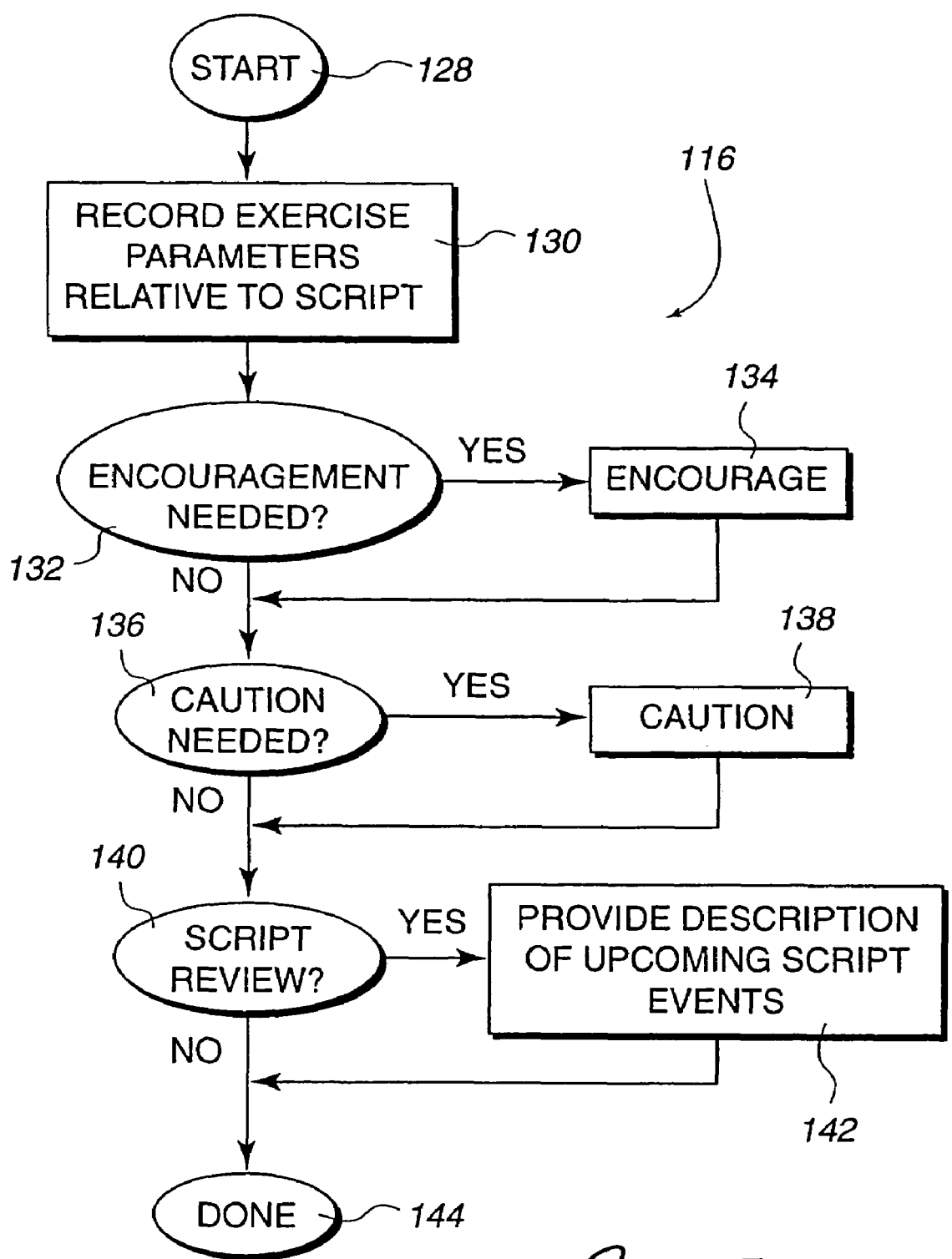
FIG. 5 is a flow diagram of the "DETECT AND RECORD USER ACTIVITY, PROVIDE FEEDBACK" step of FIG. 4.

In FIG. 5, the step 116 of FIG. 4 is explained in greater detail. Process 116 begins at 128 and, in a step 130, exercise parameters relative to the script are stored, preferably in mass storage 88. These parameters depend on the type of exercise being done, and the type of sensory input available to the system 12, but typically includes such things as time, RPM, resistance, machine state, etc. These exercise parameters are used to control the implementation of the exercise script, and are stored for later analysis.

Next, in a step 132, it is determined whether encouragement is needed. An example of encouragement being needed is when the person is slowing down below the suggested repetition rate or speed in the script or, for example, has stopped exercising entirely. In such circumstances, encouragement is given in a step 134. Again, this encouragement can be auditory via speaker 58, or visual via display 56, a combination of the two, or in any other suitable fashion. Next, in a step 136, it is determined whether a caution is needed. If so, the caution is given in a step 138 either through auditory, visual, or other ways. Caution might be needed if the user is exercising faster than that suggested by the script or if a dangerous physical condition is detected, such as by the HRM 59. Next, in a step 140, it is determined if a script preview should be provided. If yes, a step 142 provides an auditory, visual or other type of preview of upcoming script events. For example, the system 12 could be taking a user on a imaginary bicycle ride through the country. The script preview would then, in a step 142, indicate something like "We are now approaching a hill. You will note an increased resistance to pedaling in a few seconds which will steadily increase until we reach the crest of the hill in about one and a half minutes." These steps 134, 138, and 142 are further examples of the local system 12 serving as a "virtual personal trainer." The process 116 is completed at step 144.

Figure 6:
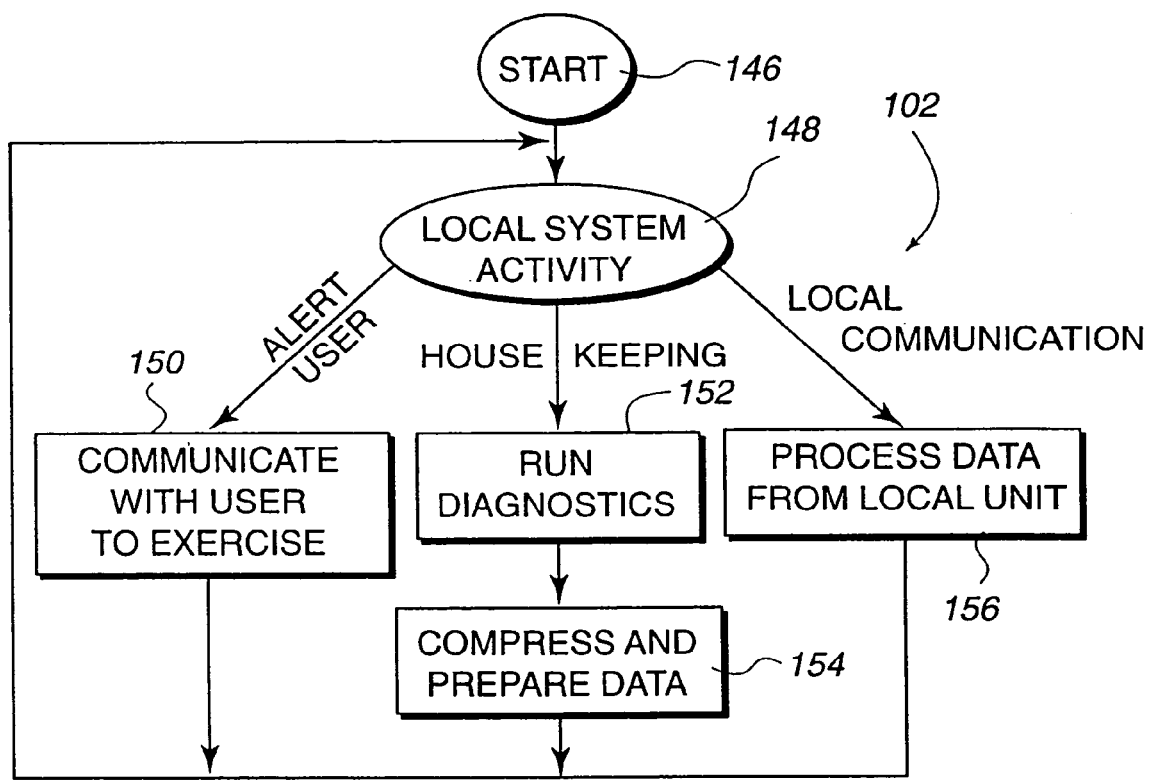
FIG. 6 is a flow diagram of a "PROCESS LOCAL SYSTEM ACTIVITY" step of FIG. 3.

In FIG. 6, step 102 of FIG. 3 is illustrated in greater detail. Process 102 begins at step 146 and, in a step 148, it is determined what type of local system activity is to be performed. Three different local system activities will be discussed herein by way of example. As a first example, the local system activity can be to alert the user as indicated in a step 150. For example, the local computer 24 can detect that it is time for a scheduled exercise session. The computer 24 can then communicate with the user via speaker 58 that it is time for a scheduled exercise. In this instance, the computer 24 would use a real time clock (RTC) 87 to know that it was time to initiate the exercise session. After completion of step 150, process control is returned to step 148.

A second type of local system activity would be housekeeping. For example, in a step 152, diagnostics can be run to check the operability and calibration of the various components of local system 12. Also, in a step 154, data compression, hard disk compaction, and data preparation can be accomplished.

A third example of local system activity detected by step 148 is a local communication within the local system 12. For example, the weight trainer 20 or the scale unit 22 might be communicating to the computer 24 via the interface 60 or vice-versa. A step 146 processes the data from the local unit accordingly and can provide commands to the local unit for the exercise or health session. Process control is then returned to step 148 after the completion of steps 150, 154, and 156.

Figure 7:
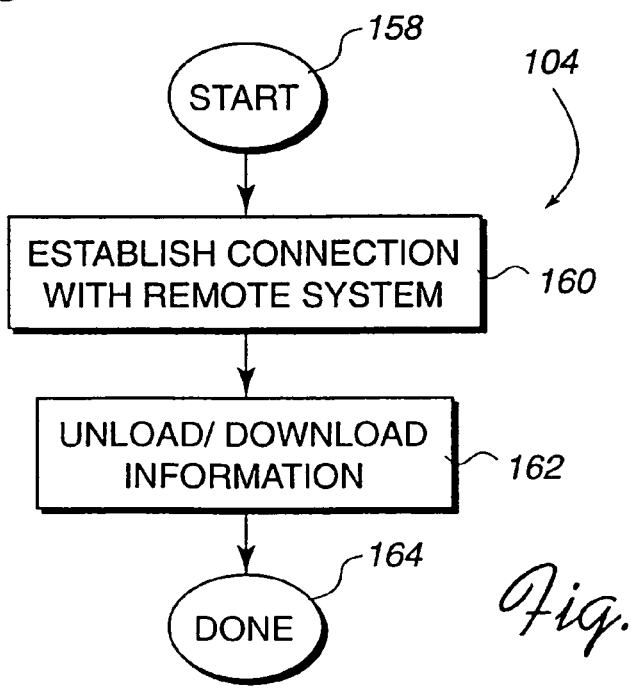
FIG. 7 is a flow diagram of the "PROCESS REMOTE ACTIVITY" step of FIG. 3.

In FIG. 7, step 104 of FIG. 3 is illustrated in greater detail. The process 104 begins at 158 and, in a step 160, the connection is established with the remote system. Next, in a step 162, information is uploaded or downloaded, the process is completed at 164. It should be noted that the connection of step 160 can be either an incoming connection or an outgoing connection. If there is an outgoing connection to a remote system computer 66 the modem 62 makes connection with the telephone line 30 and dials the telephone number of the remote system computer 66. For an incoming connection, the modem 62 detects an incoming call on telephone line 30, picks up the line, and connects to the local system computer 24.

Since the systems 12 are typically home based, the user may wish to use a single telephone line for both normal telephone needs and for use by the system 12 for step 160. It would, of course, be simpler to have an additional telephone line installed simply for the system 12, but this may be impractical from a cost point of view. If the system 12 is sharing the telephone line with the other telephones and devices in the household, mechanisms and/or processes are preferably provided to prevent interference with normal telephone usage. If the local system 12 initiates the call to the server 66, it would simply need to detect whether the telephone line was available so as not to interfere with other use of the telephone line. It can help ensure this availability by calling at unusual times, such as the middle of the night or when it is known that the user is away from the home, e.g. at work.

However, with incoming calls from a computer 66 to the computer 24 on a single home line, some way of distinguishing between calls for the local system 12 and other kinds of telephone calls should be preferably provided. Again, this could be time-based such that it is implied that a telephone call in the middle of the night is for the local system 12. The RTC 87 could be used for timing purposes in this situation, or the computer could simple start a counter. In this instance, the modem 62 would pick up the telephone quickly before other devices, such an answering machine for a facsimile machine, would have a chance to pick it up. Alternatively, the local system 12 could allow a number of "rings" before picking up the line. For example, the local system 12 could allow the telephone line 30 to ring six times before modem 62 picks up the line. In a still further instance, the computer 66 might be calling a local computer 24 and have the phone line picked up by the user or by another device (like a telephone answering machine) coupled to the telephone line 30. In this instance, the computer 66 could hang up the line and call back a second time. Since the computer 24 can monitor the line via modem 62, it could know that a call back within, for example, thirty seconds of a hang up is for the computer 24. Alternatively, it could listen to the line on the first call to determine if it was computer 66 calling, and then pick it up the line 62 immediately on any call back, or call back the remote system computer 66 itself when the telephone line was free. Again, RTC 87 can be used for timing purposes, or counters can be used, as is well known to those skilled in the art.

Information being uploaded can include parameters and data stored in the mass storage 88 concerning the exercise sessions by the user(s) of the local system 12. It can also include other system information used for diagnosing or improving the operation of the local system 12. In addition, information can be downloaded to the local system 12 from the remote system computer 66 to, for example, change exercise scripts for a user, provide upgrades for the software running on the local system computer 24, etc.

In FIG. 8, a process 166 running on a remote system computer 66 is illustrated. The process 166 begins at 168 and, in a step 170, an activity type is determined. A first type of activity is a batch system connection whereby the remote system computer 66 sequentially connects with a series of local systems for the uploading or downloading of information. This process is accomplished in step 172. A batch system connection can be used to update the software on a number of computers 24 of local system 12, or to upload exercise session data from a number of local systems 12 on a regular basis, e.g. daily, weekly, monthly, etc.

If step 170 detects a single system activity type, a step 174 connects the remote system computer 66 to a single local system 12 for uploading and/or downloading as described previously. If an activity type "PROCESS DATA" is detected by step 170, a step 176 prepares data on the computer 66 for storage, processing, communication, and/or analysis. Examples of some types of analysis of the data will be discussed subsequently with referenced to FIGS. 8a–8c. Finally, if an activity type "SERVER CONNECTION" is detected, a connection is made with the server 76 to upload or download information. The server connection can be initiated by the computer 66, or it can be initiated by the server system computer 76 depending on the circumstances. Upon the completion of any of the steps 172, 174, 176, and 178, process control is returned to step 170.

Figures 8A, 8B:
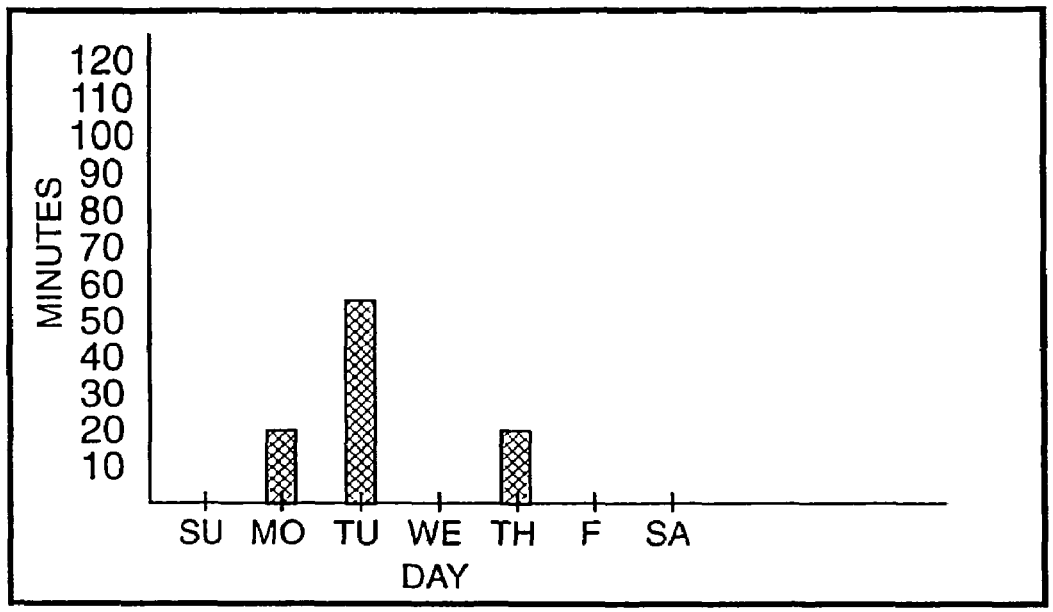
FIGS. 8a, 8b, and 8c are three examples of data analysis performed in the "PROCESS DATA" step 176 of FIG. 8.
Figure 8C:
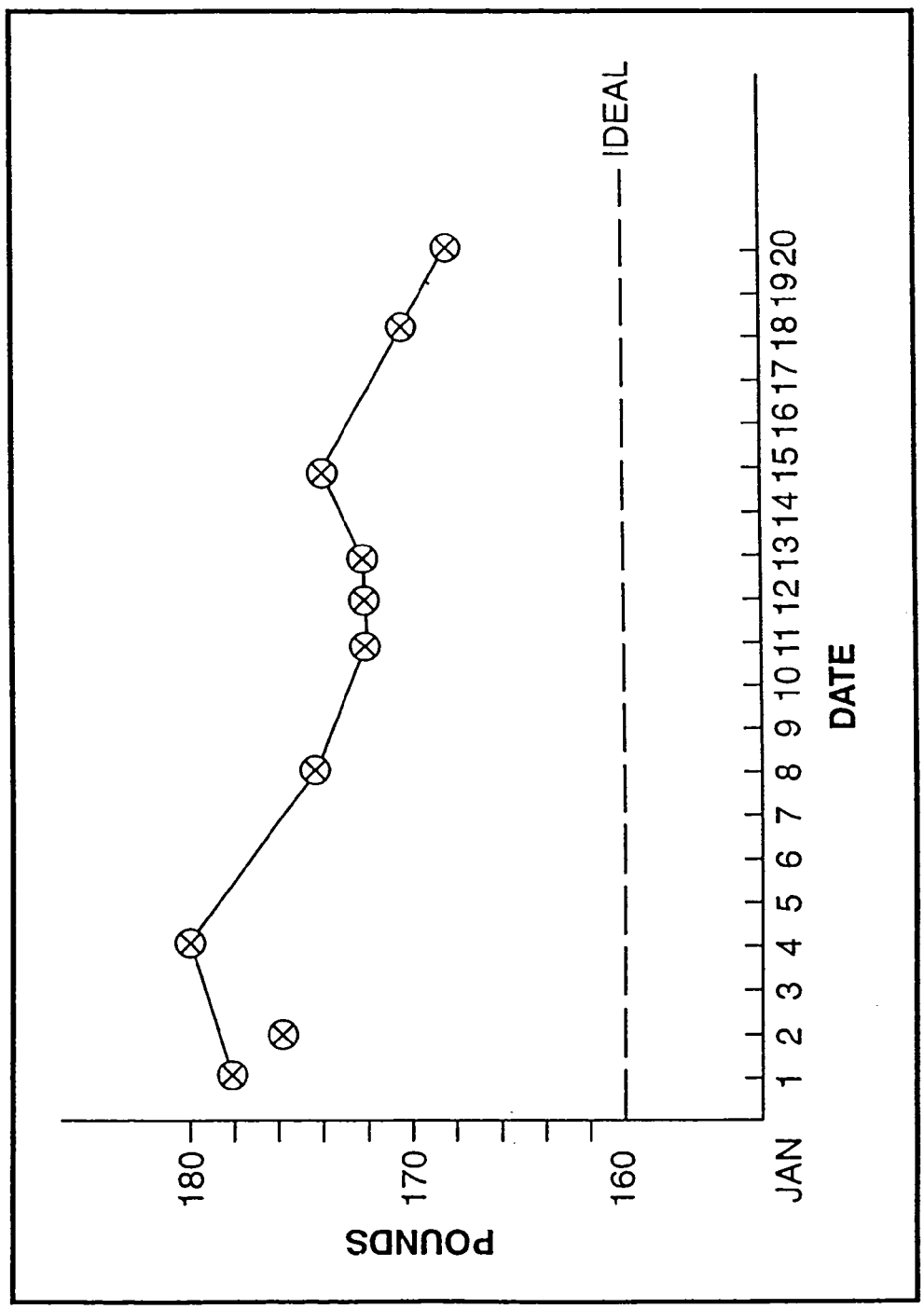

In FIGS. 8a–8c, several examples of types of data analysis that can be performed on the remote system computer 66 in step 176 of process 166 are illustrated. Of course, this analysis can be accomplished at any of the computers on the system 10 including the remote system computer 66, server system computer 76, peer system computer 78, or even on the local system computer 24. In FIG. 8a, a display of exercise activity is shown. This display can be on the display on a video display, such as a display 56, or it can be printed to make a permanent record. Along the y axis are the number of minutes of exercise, and along the x axis are the days of the week. As seen in the illustration of FIG. 8a, on Monday the user had twenty minutes of exercise, on Tuesday the user had sixty minutes of exercise, and on Thursday the user again had twenty minutes of exercise.

In FIG. 8b, another display or print out of, preferably, the remote system computer 66 is a summary of daily exercise activity. As noted, the Monday twenty minute exercise session actually consisted of a ten minute cycling session and a ten minute weight session. Also includes is a summary of the number of calories burned and other parameters associated with those activities.

In FIG. 8c, a plot of the user's weight as taken from scale 22 is shown illustrating the day-by-day weights of the user during part of the month of January. In this way, users are provided with good feed-back concerning the progress he/she is making in reaching their ideal weight. This information can be used by the remote or server systems to modify the exercise scripts and/or provide dietary counseling or products to the individual users of local stations 12.

As noted, the analysis of the data is preferably accomplished at the site of the human personal trainer, i.e. the site of the remote system computer 66. However, this analysis can also be accomplished at upstream or downstream computers. As mentioned previously, the computer 24 of the local system 12 is perfectly capable of making these types of analysis and displaying the on the display 66. Also, a simple printer I/O port can be provided in the stationary bicycle 18 to allow a printout of the graphs and charts that were shown by way of example in FIGS. 8a, 8b, and 8c.

In FIG. 9, a process 180 running on server system computer 76 is illustrated. In many ways, the process 180 running on the server system computer 76 is very similar to the process 166 running on the remote system computer 66. The process 180 begins at 182 and, in a step 184, an activity type is detected. One type of activity type is the batch connection where the server sequentially (e.g. serially and/or in parallel) connects to a series of remote system computers 66 for uploading and downloading information. This process is accomplished at step 186. Another activity type detected by step 184 is the single system connection accomplished in step 188. In step 188, the server connects to a single remote system for uploading or downloading. In the case of step 186 where there is a batch connection, the server system computer 76 will almost always be the initiating computer for the connection. With the single system connection however, the initiation of the connection can come either from the server 76 or from the remote system computer 66.

If step 184 detects a "PROCESS DATA" activity type, the data for multiple remote system computers 66 (which includes data from multiple local system 12) is prepared for storage, processing, communication, and/or analysis in a step 190. If a step 184 determines that there is to be a peer-to-peer connection with a peer server 188, a step 192 makes the connection with the peer server to pass data back and forth. Of course, there are other activity types that can be performed by the process on server system computer 76, these four being by way of example. After the completion of steps 186, 188, 190, or 192, process control is returned to step 184 to detect another activity type.

While this invention has been described in terms of several preferred embodiments, it is contemplated that alternatives, modifications, permutations and equivalents thereof will become apparent to those skilled in the art upon a reading of the specification and study of the drawings. It is therefore intended that the following appended claims be interpreted as including all such alternatives, modifications, permutations and equivalents as fall within the true spirit and scope of the present invention.

What is claimed is:

1. An exercise system comprising:
   a local system including an exercise apparatus having an actuator and an associated local computer, said local computer being able to sense a performance of a user of said exercise apparatus and control said actuator to adjust at least one operating parameter of said exercise device based on said sensed performance and a modifiable script stored on said local computer;
   a remote system including at least one remote computer; and
   an Internet connection that at least part-time couples said local system to said remote system for data communication between said local system and said remote system, such that said local computer is interposed between said remote computer and said actuator, whereby said remote system cannot directly control said actuator to adjust said at least one operating parameter of said exercise apparatus.

2. An exercise system as recited in claim 1 wherein said local system is one of a plurality of local systems, each of which is in at least part-time communication with said remote computer.

3. An exercise system as recited in claim 1 further comprising a server system including at least one server computer in at least part-time communication with said remote computer.

4. An exercise system as recited in claim 3 wherein said remote system is one of a plurality of remote systems, and each of which is in at least part-time communication with said server system.

5. An exercise system as recited in claim 1, wherein said exercise apparatus further has a sensor, said local computer being able to receive signals from said sensor, such that said local system is interposed between said remote computer and said sensor, whereby said remote system cannot directly receive signals from said sensor.

6. A local system as recited in claim 1 wherein said local computer is located internally to said exercise apparatus.

7. A local system as recited in claim 1 wherein said local computer may include at least a portion of a modified script received from said remote system.

8. A local system as recited in claim 5 wherein said exercise apparatus includes at least one of a bicycle, a rowing machine, a step machine, and a resistance trainer.

9. A local system as recited in claim 1 wherein said control may include a resistance setting for said exercise apparatus.

10. An exercise system comprising:
    a plurality of exercise apparatuses each having a moveable element for performing an exercise, wherein said plurality of exercise apparatuses comprises distinct types of exercise apparatuses;
    a local computer associated with one of said plurality of exercise apparatuses, said local computer being adapted to engage in bi-directional communication with other exercise apparatuses of said plurality of exercise apparatuses for controlling an operation of at least two of said plurality of exercise apparatuses based upon a modifiable script provided by said local computer, a remote system including at least one remote computer; and an Internet connection that at least part-time couples said local computer to said remote system for data communication between said local computer and said remote system, such that said local computer is interposed between said remote computer and said one of said plurality of exercise apparatuses, whereby said remote system cannot directly control said plurality of exercise apparatuses to adjust operating parameters of said plurality of exercise apparatuses.

11. An exercise system as recited in claim 10 wherein said local computer is located internally to one of said plurality of exercise apparatuses, and wherein said script is modifiable externally to said one of said plurality of exercise apparatus.

12. An exercise as recited in claim 11 wherein said local computer can communicate with said remote system to provide said remote system with local system data concerning said use of at least one of said plurality of exercise apparatuses, and to receive remote system data including at least a portion of a modified script to be stored in a read/write memory.

13. An exercise system as recited in claim 11 wherein said one of said plurality of exercise apparatuses includes at least one of a bicycle, a rowing machine, a step machine, and a resistance trainer.

14. An exercise system as recited in claim 12 wherein said script includes a resistance setting for at least one of said plurality of exercise apparatuses.

* * * * *

UNITED STATES PATENT AND TRADEMARK OFFICE
CERTIFICATE OF CORRECTION

PATENT NO. : 7,575,536 B1　　　　　　　　　　　　　　　　　　　　　　　　　Page 1 of 3
APPLICATION NO. : 10/729356
DATED : August 18, 2009
INVENTOR(S) : Paul L. Hickman It is certified that error appears in the above-identified patent and that said Letters Patent is hereby corrected as shown below:

Title Page
Item 56, References Cited, Other Publications, Page 4, Left Column, change "Pro Form Fitness Products Inc, Pro-Form 8.0 TXP Manual (for Model No. PF80010), Nov. 1991." to --Pro Form Fitness Products Inc, Pro-Form 8.0 TXP Manual (for Model No. PF080010), Nov. 1991.--
Item 56, References Cited, Other Publications, Page 4, Left Column, change "Icon Health And Fitness, Little Tony, One on One Video Trainer (for Model No. TLT23040), Jun. 1005." to --Icon Health And Fitness, Little Tony, One on One Video Trainer (for Model No. TLT23040), Jun. 1995.--
Item 56, References Cited, Other Publications, Page 4, Left Column, change "Icon Health And Fitness, Turn Your Treamil into an Internet Appliance With ww.iFit.com, PR Newswire, OCt, 19, 1999." to --Icon Health And Fitness, Turn Your Treadmill into an Internet Appliance With ww.iFit.com, PR Newswire, Oct, 19, 1999--
Item 56, References Cited, Other Publications, Page 4, Left Column, change "Mercuris et al, Communications of the ACM, vol. 35, No. 6, The Distributed Laboratory, Jun. 1992." to --Mercurio et al, Communications of the ACM, vol. 35, No. 6, The Distributed Laboratory, Jun. 1992.--
Item 56, References Cited, Other Publications, Page 4, Right Column, change "Forbes.com *Sweat equity*, www.forbes.com, Feb. 1998." to --Forbes.com: *Sweat equity*, www.forbes.com, Feb. 1998.--
Item 56, References Cited, Other Publications, Page 5, Left Column, change "Restriction requirement dated Aor. 17, 2007, 5 pages, U.S. Appl. No. 11/429,858." to --Restriction requirement dated Apr. 17, 2007, 5 pages, U.S. Appl. No. 11/429,858.--
Item 56, References Cited, Other Publications, Page 5, Left Column, change "Restriction Requirement dated Sep. 21, 2004, 4 pages, U.S. Appl. No. 10/106,824." to --Restriction Requirement dated Sep. 21, 2004, 4 pages, U.S. Appl. No. 10/106,842.--
Item 56, References Cited, Other Publications, Page 5, Right Column, change "Notice of Allowance and Fee(s) Due, date mailed Apr. 17, 200, 4 pages, U.S. Appl. No. 10/773,617." to --Notice of Allowance and Fee(s) Due, date mailed Apr. 17, 2006, 4 pages, U.S. Appl. No. 10/773,617.--
Item 56, References Cited, Other Publications, Page 5, Right Column, change "Notice of Allowance and Fee(s) Due, date mailed Jul. 6, 2006, 4 pages, U.S. Appl. No. 10773,617." to --Notice of Allowance and Fee(s) Due, date mailed Jul. 6, 2006, 4 pages, U.S. Appl. No. 10/773,617.--

Drawings
Sheet 2, replace FIG. 2 with the figure depicted below, wherein computer 80 and bus 92 are labeled
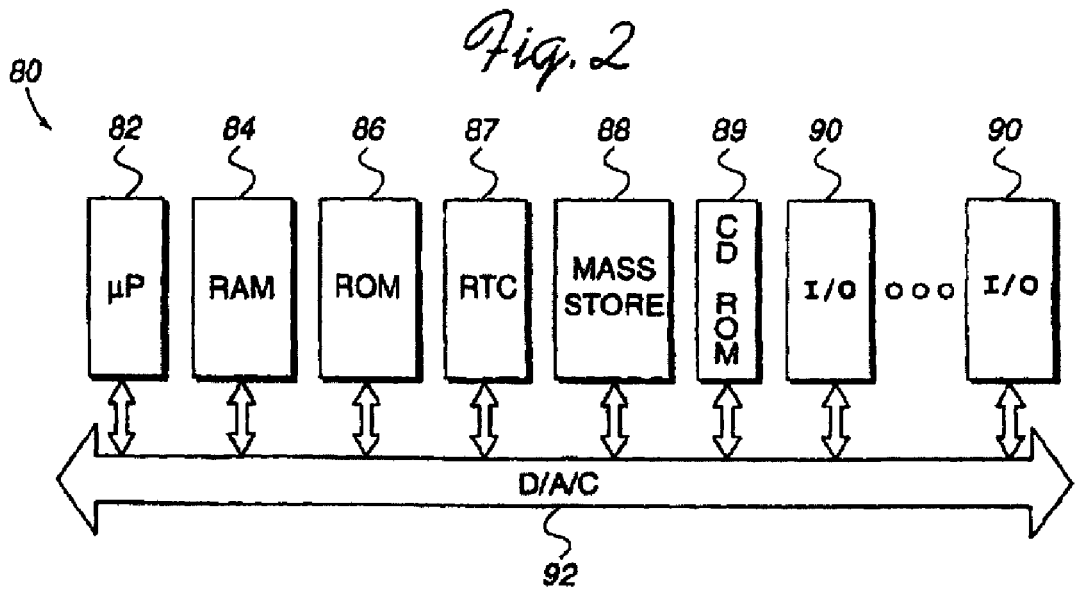
Sheet 3, replace FIG. 4 with the figure depicted below, wherein step 100 is labeled
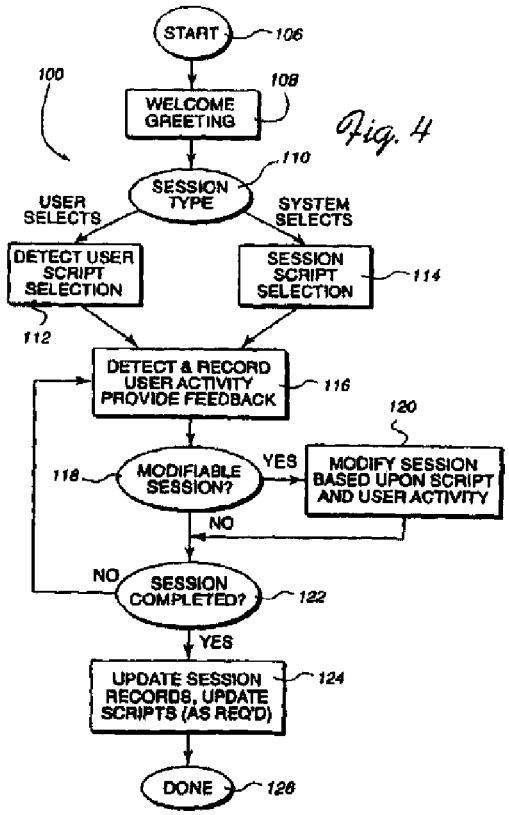

CERTIFICATE OF CORRECTION (continued)
U.S. Pat. No. 7,575,536 B1

Column 4
Line 28, change "handle bar 34" to --handle bar 44--
Line 44, change "scale." to --scale 22.--
Line 66, change "computer" to --computer 24--
Line 67, change "bicycle." to --bicycle 18.--

Column 5
Line 1, change "computer" to --computer 24--
Line 7, change "bicycle" to --bicycle 18--
Line 26, change "This additional" to --These additional--
Line 26, after "either" insert --be--
Line 28, change "full fledged computer system" to --a full-fledged computer system,--
Line 33, change "58" to --58,--
Line 39, change "control" to --controlled--
Line 39, change "52" to --52,--

Column 6
Line 9, change "link" to --link,--

Column 8
Line 61, change "or visual" to --visual--

Column 10
Line 11, change "computer" to --computer 24--
Line 13, change "for" to --or--

Column 11
Line 26, change "feed-back" to --feedback--
Line 64, remove [188]

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO.       : 7,575,536 B1                                                Page 1 of 1
APPLICATION NO.  : 10/729356
DATED            : August 18, 2009
INVENTOR(S)      : Paul L. Hickman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 31 days.

Signed and Sealed this

Seventh Day of September, 2010

David J. Kappos
*Director of the United States Patent and Trademark Office*